US011813333B2

(12) United States Patent
Lai et al.

(10) Patent No.: US 11,813,333 B2
(45) Date of Patent: Nov. 14, 2023

(54) USE OF HIGH MOLECULAR WEIGHT POLYETHYLENE GLYCOL COMPOSITIONS TO RESTORE THE EFFICACY OF PEGYLATED THERAPEUTIC COMPOSITIONS

(71) Applicant: THE UNIVERSITY OF NORTH CAROLINA AT CHAPEL HILL, Chapel Hill, NC (US)

(72) Inventors: Samuel Lai, Carrboro, NC (US); Morgan McSweeney, Cary, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 237 days.

(21) Appl. No.: 16/642,722

(22) PCT Filed: Aug. 27, 2018

(86) PCT No.: PCT/US2018/048126
§ 371 (c)(1),
(2) Date: Feb. 27, 2020

(87) PCT Pub. No.: WO2019/046185
PCT Pub. Date: Mar. 7, 2019

(65) Prior Publication Data
US 2020/0254107 A1 Aug. 13, 2020

Related U.S. Application Data

(60) Provisional application No. 62/550,847, filed on Aug. 28, 2017.

(51) Int. Cl.
A61K 47/60 (2017.01)
A61K 9/127 (2006.01)
A61K 45/06 (2006.01)

(52) U.S. Cl.
CPC ............ *A61K 47/60* (2017.08); *A61K 9/1271* (2013.01); *A61K 45/06* (2013.01)

(58) Field of Classification Search
CPC .............................. A61K 9/1271; A61K 47/60
See application file for complete search history.

(56) References Cited

FOREIGN PATENT DOCUMENTS

WO WO 2017/099823 A1 6/2017

OTHER PUBLICATIONS

Dams et al (JPET, 2000; 292(3):1071-1079). (Year: 2000).*
International Search Report and Written Opnion for PCT/US2018/048126, dated Oct. 10, 2018. 15 pages.
Amselem et al., Optimization and upscaling of doxorubicin-containing liposomes for clinical use. J Pharm Sci. Dec. 1990;79(12):1045-52.
Anders et al., Pharmacokinetics and efficacy of PEGylated liposomal doxorubicin in an intracranial model of breast cancer. PLoS One. May 1, 2013;8(5):e61359. 10 pages.
Armstrong et al., Antibody against poly(ethylene glycol) adversely affects PEG-asparaginase therapy in acute lymphoblastic leukemia patients. Cancer. Jul. 1, 2007;110(1):103-11.
Fix et al., Accelerated Clearance of Ultrasound Contrast Agents Containing Polyethylene Glycol is Associated with the Generation of Anti-Polyethylene Glycol Antibodies. Ultrasound Med Biol, 2018. 44(6): p. 1266-1280.
Gabizon et al., Pharmacokinetics and tissue distribution of doxorubicin encapsulated in stable liposomes with long circulation times. J Natl Cancer Inst. Oct. 4, 1989;81(19):1484-8.
Ganson et al., Pre-existing anti-polyethylene glycol antibody linked to first-exposure allergic reactions to pegnivacogin, a PEGylated RNA aptamer. J Allergy Clin Immunol, 2016. 137(5): p. 1610-1613. e7.
Garay et al., Antibodies against polyethylene glycol in healthy subjects and in patients treated with PEG-conjugated agents. Expert Opin Drug Deliv, 2012. 9(11): p. 1319-23.
Gefen et al., The impact of PEGylation on protein immunogenicity. Int Immunopharmacol. Feb. 2013;15(2):254-9.
Hershfield et al., Induced and pre-existing anti-polyethylene glycol antibody in a trial of every 3-week dosing of pegloticase for refractory gout, including in organ transplant recipients. Arthritis Res Ther. Mar. 7, 2014;16(2):R63. 11 pages.
Herzberger et al., Polymerization of Ethylene Oxide, Propylene Oxide, and Other Alkylene Oxides: Synthesis, Novel Polymer Architectures, and Bioconjugation. Chem Rev. Feb. 24, 2016;116(4):2170-243.
Hsieh et al., Pre-existing anti-polyethylene glycol antibody reduces the therapeutic efficacy and pharmacokinetics of PEGylated liposomes. Theranostics. May 9, 2018;8(11):3164-3175.
Ishida et al., Accelerated blood clearance of PEGylated liposomes upon repeated injections: effect of doxorubicin-encapsulation and high-dose first injection. J Control Release. Oct. 27, 2006;115(3):251-8.
Jevsevar et al., PEGylation of therapeutic proteins. Biotechnol J. Jan. 2010;5(1):113-28.
Jokerst et al., Nanoparticle PEGylation for imaging and therapy. Nanomedicine (Lond). Jun. 2011;6(4):715-28.

(Continued)

*Primary Examiner* — Marcos L Sznaidman
*Assistant Examiner* — Rayna Rodriguez
(74) *Attorney, Agent, or Firm* — Casimir Jones SC; Lisa Mueller

(57) ABSTRACT

The present disclosure relates to methods of reducing accelerated blood clearance of at least one pegylated therapeutic composition in a subject suffering from a disease and in need of treatment. The methods involve administering at least one high molecular weight polyethylene glycol composition to a subject suffering from a disease. The administration of at least one high molecular weight polyethylene glycol composition can also be used to increase the circulation half-life of at least one pegylated therapeutic composition as well as restore the pharmacokinetics of the pegylated therapeutic composition in a subject having a high titer of anti-polyethylene glycol antibodies.

14 Claims, 13 Drawing Sheets

(56) References Cited

OTHER PUBLICATIONS

Lipsky et al., Pegloticase immunogenicity: the relationship between efficacy and antibody development in patients treated for refractory chronic gout. Arthritis Res Ther. Mar. 4, 2014;16(2):R60. 8 pages.
McSweeney et al., A minimal physiologically based pharmacokinetic model that predicts anti-PEG IgG-mediated clearance of PEGylated drugs in human and mouse. J Control Release. Aug. 28, 2018;284:171-178.
Milla et al., PEGylation of proteins and liposomes: a powerful and flexible strategy to improve the drug delivery. Curr Drug Metab. Jan. 2012;13(1):105-19.
Mima et al., Anti-PEG IgM Is a Major Contributor to the Accelerated Blood Clearance of Polyethylene Glycol-Conjugated Protein. Mol Pharm, 2015. 12(7): p. 2429-35.
Moghimi, Re-establishing the long cirulatory behavior of poloxamine-coated particles after repeated intravenous administraion: applications in cancer drug delivery and imaging. Biochim Biophys Acta. Oct. 18, 1999;1472(1-2):399-403.
Plant et al., Low-Volume Resuscitation for Hemorrhagic Shock: Understanding the Mechanism of PEG-20k. J Pharmacol Exp Ther, 2017. 361(2): p. 334-340.
Plant et al., Low-volume resuscitation using polyethylene glycol-20k in a preclinical porcine model of hemorrhagic shock. J Trauma Acute Care Surg, 2016. 81(6): p. 1056-1062.
Povsic et al., Pre-existing anti-PEG antibodies are associated with severe immediate allergic reactions to pegnivacogin, a PEGylated aptamer. J Allergy Clin Immunol. Dec. 2016;138(6):1712-1715.
Richter et al., Antibodies against polyethylene glycol produced in animals by immunization with monomethoxy polyethylene glycol modified proteins. Int Arch Allergy Appl Immunol, 1983. 70(2): p. 124-31.
Toong et al., Clearing the complexity: immune complexes and their treatment in lupus nephritis. Int J Nephrol Renovasc Dis. 2011;4:17-28.
Turecek et al., PEGylation of Biopharmaceuticals: A Review of Chemistry and Nonclinical Safety Information of Approved Drugs. J Pharm Sci. Feb. 2016;105(2):460-475.
Veronese et al., The impact of PEGylation on biological therapies. BioDrugs, 2008. 22(5): p. 315-29.
Veronese et al., PEGylation, successful approach to drug delivery. Drug Discov Today. Nov. 1, 2005;10(21):1451-8.
Vivaldo-Lima et al., An Updated Review on Suspension Polymerization. Industrial & Engineering Chemistry Research, 1997. 36(4): p. 939-965.
Yamaoka et al., Distribution and tissue uptake of poly(ethylene glycol) with different molecular weights after intravenous administration to mice. J Pharm Sci, 1994. 83(4): p. 601-6.
Yang et al., Anti-PEG immunity; emergence, characteristics and unaddressed questions. Wiley Interdiscip Rev Nanomed Nanobiotechnol. Sep.-Oct. 2015;7(5):655-77.
Zamboni et al., Plasma, tumor, and tissue disposition of STEALTH liposomal CKD-602 (S-CKD602) and nonliposomal CKD-602 in mice bearing A375 human melanoma xenografts. Clin Cancer Res. Dec. 1, 2007;13(23):7217-23.

* cited by examiner

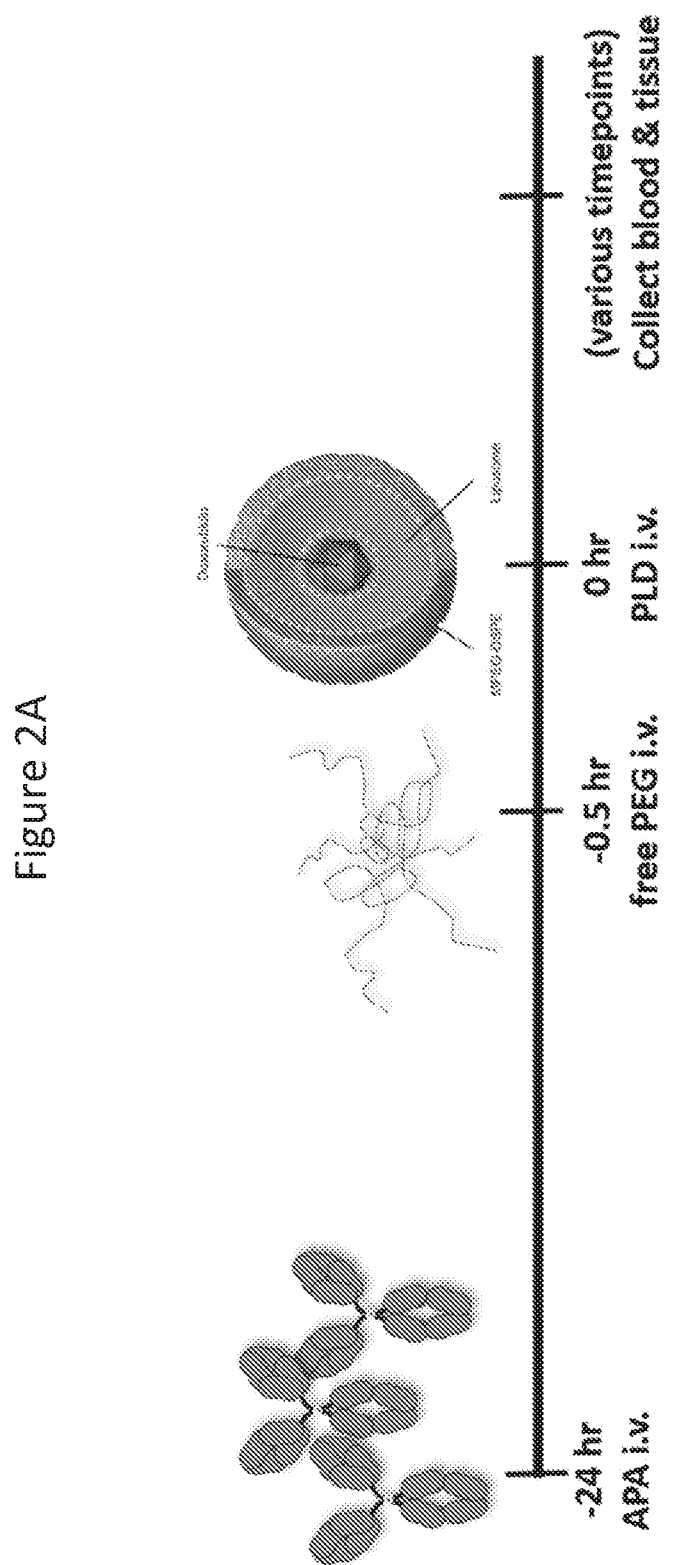

|  | Control | +free PEG |
|---|---|---|
| IHC score | | |
| IgG | 0.5 | 0.5 |
| IgM | 1 | 1 |
| C3 | 0.5 | 0.5 |
| PEG | 0 | 0 |

USE OF HIGH MOLECULAR WEIGHT POLYETHYLENE GLYCOL COMPOSITIONS TO RESTORE THE EFFICACY OF PEGYLATED THERAPEUTIC COMPOSITIONS

GOVERNMENT FUNDING

This invention was made with government support under Grant Number HL141934 awarded by the National Institutes of Health. The government has certain rights in the invention.

RELATED APPLICATION INFORMATION

This application is a national phase application under 35 U.S.C. § 371 of PCT International Application No. PCT/US2018/048126, filed Aug. 27, 2018, which claims priority to U.S. Patent Application No. 62/550,8471 filed on Aug. 28, 2017, the contents of which are herein incorporated by reference.

FIELD

The present disclosure relates to methods of reducing accelerated blood clearance of at least one pegylated therapeutic composition in a subject suffering from a disease and in need of treatment. The methods involve administering at least one high molecular weight polyethylene glycol composition to a subject suffering from a disease. Specifically, the high molecular weight polyethylene glycol in the high molecular weight polyethylene glycol composition has a molecular weight of between about 20 kDa to about 200 kDa. Additionally, the high molecular weight polyethylene glycol composition can be administered prior to or simultaneously with the administration of the at least one pegylated therapeutic composition. Moreover, the administration of at least one high molecular weight polyethylene glycol composition can also be used to increase the circulation half-life of at least one pegylated therapeutic composition as well as restore the pharmacokinetics of the pegylated therapeutic composition in a subject having a high titer of anti-polyethylene glycol antibodies.

BACKGROUND

The ability of polyethylene glycol (PEG) to improve the pharmacokinetic profile of various protein and nanoparticle therapeutic compositions has led to its popular use in a wide variety of drug products (See, Veronese, F.M. and G. Pasut, PEGylation, successful approach to drug delivery. Drug Discov Today, 2005. 10(21): p. 1451-8; Milla, P., F. Dosio, and L. Cattel, PEGylation of proteins and liposomes: a powerful and flexible strategy to improve the drug delivery. Curr Drug Metab, 2012. 13(1): p. 105-19; Jokerst, J. V., et al., Nanoparticle PEGylation for imaging and therapy. Nanomedicine (Lond), 2011. 6(4): p. 715-28). PEGylated therapeutic compositions typically exhibit prolonged circulation kinetics and decreased immunogenicity (See, Veronese, F.M. and G. Pasut, PEGylation, successful approach to drug delivery. Drug Discov Today, 2005. 10(21): p. 1451-8). PEGylation of drug molecules reduces rapid renal clearance by increasing the hydrodynamic sizes above the renal filtration threshold and increasing the aqueous solubility of hydrophobic drugs, thus improving colloidal stability and reducing aggregation (See, Veronese, F.M. and A. Mero, The impact of PEGylation on biological therapies. BioDrugs, 2008. 22(5): p. 315-29.). As PEG chains are highly flexible, they can also sterically inhibit interactions with immune system blood components, such as opsonins and degradative enzymes (Id.). This frequently reduces the immunogenicity and antigenicity compared to the underlying therapeutic drugs or particles (See, Gefen, T., et al., The impact of PEGylation on protein immunogenicity. Int Immunopharmacol, 2013. 15(2): p. 254-9). These various "stealth" effects of PEG grafting enable less frequent dosing to patients, increased safety, and improved therapeutic outcomes.

Although PEGylation is intended to increase the half-life of drugs, the repeated injection of PEGylated liposomes and select PEGylated proteins can cause subsequent injections to be rapidly eliminated from circulation, a phenomenon called the accelerated blood clearance (ABC) effect (See, Mima, Y., et al., Anti-PEG IgM Is a Major Contributor to the Accelerated Blood Clearance of Polyethylene Glycol-Conjugated Protein. Mol Pharm, 2015. 12(7): p. 2429-35; Richter, A.W. and E. Akerblom, Antibodies against polyethylene glycol produced in animals by immunization with monomethoxy polyethylene glycol modified proteins. Int Arch Allergy Appl Immunol, 1983. 70(2): p. 124-31; Ishida, T., et al., Accelerated blood clearance of PEGylated liposomes upon repeated injections: effect of doxorubicin-encapsulation and high-dose first injection. J Control Release, 2006. 115(3): p. 251-8.). The association of ABC with anti-PEG antibodies has now been extensively documented for several PEGylated therapeutics in clinical settings (See, Lipsky, P. E., et al., Pegloticase immunogenicity: the relationship between efficacy and antibody development in patients treated for refractory chronic gout. Arthritis Res Ther, 2014. 16(2): p. R60; Hershfield, M. S., et al., Induced and pre-existing anti-polyethylene glycol antibody in a trial of every 3-week dosing of pegloticase for refractory gout, including in organ transplant recipients. Arthritis Research & Therapy, 2014. 16(2): p. R63-R63; Armstrong, J. K., et al., Antibody against polyethylene glycol) adversely affects PEG-asparaginase therapy in acute lymphoblastic leukemia patients. Cancer, 2007. 110(1): p. 103-11; Ganson, N.J., et al., Pre-existing anti-polyethylene glycol antibody linked to first-exposure allergic reactions to pegnivacogin, a PEGylated RNA aptamer. J Allergy Clin Immunol, 2016. 137(5): p. 1610-1613.e7; Povsic, T. J., et al., Pre-existing anti-PEG antibodies are associated with severe immediate allergic reactions to pegnivacogin, a PEGylated aptamer. Journal of Allergy and Clinical Immunology, 2016. 138(6): p. 1712-1715; Garay, R. P., et al., Antibodies against polyethylene glycol in healthy subjects and in patients treated with PEG-conjugated agents. Expert Opin Drug Deliv, 2012. 9(11): p. 1319-23). For example, in a study of PEG-asparaginase, roughly one-third of treated patients were found to be APA-positive by serology and APA were associated with poor therapeutic efficacy (See, Armstrong, J. K., et al., Antibody against polyethylene glycol) adversely affects PEG-asparaginase therapy in acute lymphoblastic leukemia patients. Cancer, 2007. 110(1): p. 103-11.). Similarly, about one-third of patients with chronic refractory gout that were on a pegloticase regimen developed APA that led to rapid clearance of the enzyme from the blood (Lipsky, P. E., et al., Pegloticase immunogenicity: the relationship between efficacy and antibody development in patients treated for refractory chronic gout. Arthritis Res Ther, 2014. 16(2): p. R60; Hershfield, M. S., et al., Induced and pre-existing anti-polyethylene glycol antibody in a trial of every 3-week dosing of pegloticase for refractory gout, including in organ transplant recipients. Arthritis Research & Therapy, 2014.

16(2): p. R63-R63.). Additionally, it was recently found that the repeated administration of PEGylated microbubbles (Definity™, an ultrasound contrast enhancing agent) also led to rapid clearance of subsequent doses of Definity in rats (See, Fix, S. M., et al., Accelerated Clearance of Ultrasound Contrast Agents Containing Polyethylene Glycol is Associated with the Generation of Anti-Polyethylene Glycol Antibodies. Ultrasound Med Biol, 2018. 44(6): p. 1266-1280.). In addition to infusion reactions, APA has been associated with serious adverse events, including those that contributed to discontinuation of PEGylated RNA aptamer pegnivacogin in phase III clinical trials (See, Ganson, N.J., et al., Pre-existing anti-polyethylene glycol antibody linked to first-exposure allergic reactions to pegnivacogin, a PEGylated RNA aptamer. J Allergy Clin Immunol, 2016. 137(5): p. 1610-1613.e7; Povsic, T. J., et al., Pre-existing anti-PEG antibodies are associated with severe immediate allergic reactions to pegnivacogin, a PEGylated aptamer. Journal of Allergy and Clinical Immunology, 2016. 138(6): p. 1712-1715.).

With the large number of PEGylated therapeutic compositions that are approved or in clinical development and the high costs of bringing alternative treatments to the market, there is a need to enable the safe use of PEGylated therapeutic compositions in patients who produce high levels of APA. More specifically, there is a need for methods of reducing the ABC of pegylated therapeutic compositions (and thus improving or increasing their circulation half-life and restoring their pharmacokinetics) by anti-PEG antibodies in subjects or patients suffering from a disease and in need of treatment or continued treatment thereof.

SUMMARY

In one aspect, the present disclosure relates to a method of reducing accelerated blood clearance of at least one pegylated therapeutic composition by anti-PEG antibodies in a subject suffering from a disease and in need of treatment thereof. Specifically, the method comprises the step of administering from about 0.1 to about 500 milligrams per kilogram of at least one high molecular weight polyethylene glycol (PEG) composition to a subject suffering from a disease and in need of treatment with the at least one pegylated therapeutic composition.

The high molecular weight PEG composition used in the above method can be administered prior to the administration of the at least one pegylated therapeutic composition. Alternatively, the high molecular weight PEG composition can be administered simultaneously with the at least one pegylated therapeutic composition. For example, in this aspect, the high molecular weight PEG composition can be co-administered with the at least one pegylated therapeutic composition.

As mentioned above, the high molecular weight PEG composition can be administered to the subject in an amount of from about 0.1 to about 500 milligrams per kilogram. Alternatively, the high molecular weight PEG composition can be administered to the subject in an amount of from about 0.5 to about 400 milligrams per kilogram. Still further alternatively, the high molecular weight PEG composition can be administered in an amount of 1.0 to about 250 milligrams per kilogram.

Any high molecular weight PEG having a molecular weight between about 20 kDa to about 200 kDa can be used in the high molecular weight PEG composition and the above method. In one aspect, the high molecular weight PEG has a molecular weight between about 20 kDa to about 200 kDa. In one aspect, the high molecular weight PEG has a molecular weight between about 20 kDa to about 190 kDa. In one aspect, the high molecular weight PEG has a molecular weight between about 20 kDa to about 180 kDa. In one aspect, the high molecular weight PEG has a molecular weight between about 20 kDa to about 170 kDa. In one aspect, the high molecular weight PEG has a molecular weight between about 20 kDa to about 160 kDa. In one aspect, the high molecular weight PEG has a molecular weight between about 20 kDa to about 150 kDa. In one aspect, the high molecular weight PEG has a molecular weight between about 20 kDa to about 140 kDa. In one aspect, the high molecular weight PEG has a molecular weight between about 20 kDa to about 130 kDa. In one aspect, the high molecular weight PEG has a molecular weight between about 20 kDa to about 120 kDa. In one aspect, the high molecular weight PEG has a molecular weight between about 20 kDa to about 110 kDa. In one aspect, the high molecular weight PEG has a molecular weight between about 20 kDa to about 100 kDa. In one aspect, the high molecular weight PEG has a molecular weight between about 20 kDa to about 90 kDa. In another aspect, the high molecular weight PEG has a molecular weight between about 20 kDa to about 80 kDa. In another aspect, the high molecular weight PEG has a molecular weight between about 20 kDa to about 70 kDa. In another aspect, the high molecular weight PEG has a molecular weight between about 20 kDa to about 60 kDa. In another aspect, the high molecular weight PEG has a molecular weight between about 20 kDa to about 50 kDa. In another aspect, the high molecular weight PEG has a molecular weight between about 20 kDa to about 40 kDa. In yet another aspect, the high molecular weight PEG can have a molecular weight of about 20 kDa, about 25 kDa, about 30 kDa, about 40 kDa, about kDa, about 60 kDa, about 70 kDa, about 75 kDa, about 80 kDa, about 90 kDa, about 100 kDa, about 110 kDa, about 120 kDa, about 130 kDa, about 140 kDa, about 150 kDa, about 160 kDa, about 170 kDa, about 180 kDa, about 190 kDa or about 200 kDa or combinations thereof.

In one aspect, the high molecular weight PEG used in the high molecular weight PEG composition and in above method can have a geometry that is linear. In another aspect, the high molecular weight PEG can have a geometry that is branched. In yet another aspect, the high molecular weight PEG has a geometry that is star-shaped. In still yet another aspect, the high molecular weight PEG has a geometry that is comb-shaped.

In aspects when the high molecular weight PEG composition is to be administered to the subject prior to the administration of at least one pegylated therapeutic composition, the at least one high molecular weight PEG composition can be administered at least 30 seconds, at least 60 seconds, at least 90 seconds, at least 2 minutes, at least 3 minutes, at least 4 minutes, at least 5 minutes, at least 10 minutes, at least 15 minutes, at least 20 minutes, at least 25 minutes, at least 30 minutes, at least 40 minutes, at least 45 minutes, at least 50 minutes, at least 60 minutes, at least 90 minutes, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours prior to administration of the at least one pegylated therapeutic composition.

Any type of pegylated therapeutic composition can be used in the above method. For example, the at least one pegylated therapeutic composition can comprise at least one protein, peptide, antibody, enzyme, liposome, aptamer, dendrimer, polymeric particle, micelle, inorganic nanoparticle or combinations thereof. In one aspect, the at least one pegylated therapeutic composition comprises a protein. In another aspect, the at least one pegylated therapeutic composition comprises a peptide. In yet another aspect, the at least one pegylated therapeutic composition comprises an antibody (such as a monoclonal antibody, a chimeric antibody, a humanized antibody, a fully human antibody, a bi-specific antibody, a multi-specific antibody, an antibody fragment, or combinations thereof). In another aspect, the at least one pegylated therapeutic composition comprises an enzyme. In still yet another aspect, the at least one pegylated therapeutic comprises a dendrimer. In still yet another aspect, the at least one pegylated therapeutic composition comprises a liposome. In still yet another aspect, the at least one pegylated therapeutic composition comprises a polymeric particle. In still yet another embodiment, the at least one pegylated therapeutic composition comprises a micelle. In still yet another aspect, the at least one pegylated therapeutic composition comprises an inorganic nanoparticle. In another aspect, the present disclosure relates to a method of increasing the circulation half-life of at least one pegylated therapeutic composition to be repeatedly administered to a subject suffering from a disease. The method comprises the step of administering from about 1 to about 2500 milligrams per kilogram of at least one high molecular weight polyethylene glycol composition to a subject that has previously been administered at least one pegylated therapeutic composition or that is known to possess a high titer of pre-existing anti-PEG antibodies. The high molecular weight PEG composition used in the above method can be administered prior to the administration of the at least one pegylated therapeutic composition (or repeated or subsequent administration thereof). Alternatively, the high molecular weight PEG composition can be administered simultaneously with any subsequent or further administration of the at least one pegylated therapeutic composition. For example, in this aspect, the high molecular weight PEG composition can be co-administered with the at least one pegylated therapeutic composition.

As mentioned above, the high molecular weight PEG composition can be administered to the subject in an amount of from about 1 to about 2500 milligrams per kilogram. Alternatively, the high molecular weight PEG composition can be administered to the subject in an amount of from about 50 to about 2200 milligrams per kilogram. Still further alternatively, the high molecular weight PEG composition can be administered in an amount of 100 to about 2000 milligrams per kilogram.

Any high molecular weight PEG having a molecular weight between about 20 kDa to about 200 kDa can be used in the high molecular weight PEG composition and the above method. In one aspect, the high molecular weight PEG has a molecular weight between about 20 kDa to about 200 kDa. In one aspect, the high molecular weight PEG has a molecular weight between about 20 kDa to about 190 kDa. In one aspect, the high molecular weight PEG has a molecular weight between about 20 kDa to about 180 kDa. In one aspect, the high molecular weight PEG has a molecular weight between about 20 kDa to about 170 kDa. In one aspect, the high molecular weight PEG has a molecular weight between about 20 kDa to about 160 kDa. In one aspect, the high molecular weight PEG has a molecular weight between about 20 kDa to about 150 kDa. In one aspect, the high molecular weight PEG has a molecular weight between about 20 kDa to about 140 kDa. In one aspect, the high molecular weight PEG has a molecular weight between about 20 kDa to about 130 kDa. In one aspect, the high molecular weight PEG has a molecular weight between about 20 kDa to about 120 kDa. In one aspect, the high molecular weight PEG has a molecular weight between about 20 kDa to about 110 kDa. In one aspect, the high molecular weight PEG has a molecular weight between about 20 kDa to about 100 kDa. In one aspect, the high molecular weight PEG has a molecular weight between about 20 kDa to about 90 kDa. In another aspect, the high molecular weight PEG has a molecular weight between about 20 kDa to about 80 kDa. In another aspect, the high molecular weight PEG has a molecular weight between about 20 kDa to about 70 kDa. In another aspect, the high molecular weight PEG has a molecular weight between about 20 kDa to about 60 kDa. In another aspect, the high molecular weight PEG has a molecular weight between about 20 kDa to about 50 kDa. In another aspect, the high molecular weight PEG has a molecular weight between about 20 kDa to about 40 kDa. In yet another aspect, the high molecular weight PEG can have a molecular weight of about 20 kDa, about 25 kDa, about 30 kDa, about 40 kDa, about 50 kDa, about 60 kDa, about 70 kDa, about 75 kDa, about 80 kDa, about 90 kDa, about 100 kDa, about 110 kDa, about 120 kDa, about 130 kDa, about 140 kDa, about 150 kDa, about 160 kDa, about 170 kDa, about 180 kDa, about 190 kDa or about 200 kDa or combinations thereof.

In one aspect, the high molecular weight PEG used in the high molecular weight PEG composition and in the above method can have a geometry that is linear. In another aspect, the high molecular weight PEG can have a geometry that is branched. In yet another aspect, the high molecular weight PEG has a geometry that is star-shaped. In still yet another aspect, the high molecular weight PEG has a geometry that is comb-shaped.

In aspects when the high molecular weight PEG composition is to be administered to the subject prior to the administration of at least one pegylated therapeutic composition, the at least one high molecular weight PEG composition can be administered at least 30 seconds, at least 60 seconds, at least 90 seconds, at least 2 minutes, at least 3 minutes, at least 4 minutes, at least 5 minutes, at least 10 minutes, at least 15 minutes, at least 20 minutes, at least 25 minutes, at least 30 minutes, at least 40 minutes, at least 45 minutes, at least 50 minutes, at least 60 minutes, at least 90 minutes, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours prior to administration of the at least one pegylated therapeutic composition.

Any type of pegylated therapeutic composition can be used in the above method. For example, the at least one pegylated therapeutic composition can comprise at least one protein, peptide, antibody, enzyme, liposome, aptamer, dendrimer, polymeric particle, micelle, inorganic nanoparticle or combinations thereof. In one aspect, the at least one pegylated therapeutic composition comprises a protein. In another aspect, the at least one pegylated therapeutic composition comprises a peptide. In yet another aspect, the at least one pegylated therapeutic composition comprises an antibody (such as a monoclonal antibody, a chimeric antibody, a humanized antibody, a fully human antibody, a bi-specific antibody, a multi-specific antibody, an antibody fragment or combinations thereof). In another aspect, the at least one pegylated therapeutic composition comprises an enzyme. In still yet another aspect, the at least one pegylated therapeutic comprises a dendrimer. In still yet another aspect, the at least one pegylated therapeutic composition comprises a liposome. In still yet another aspect, the at least one pegylated therapeutic composition comprises a polymeric particle. In still yet another embodiment, the at least one pegylated therapeutic composition comprises a micelle. In still yet another aspect, the at least one pegylated therapeutic composition comprises an inorganic nanoparticle.

In still yet a further aspect, the present disclosure relates to a method of restoring the pharmacokinetics of at least one pegylated therapeutic composition that will be repeatedly administered to a subject suffering from a disease. The method comprises the step of administering from about 1 to about 2500 milligrams per kilogram of at least one high molecular weight polyethylene glycol composition to a subject that has previously been administered at least one pegylated therapeutic composition.

The high molecular weight PEG composition used in the above method can be administered prior to the administration of the at least one pegylated therapeutic composition (or repeated or subsequent administration thereof). Alternatively, the high molecular weight PEG composition can be administered simultaneously with any subsequent or further administration of the at least one pegylated therapeutic composition. For example, in this aspect, the high molecular weight PEG composition can be co-administered with the at least one pegylated therapeutic composition.

Additionally, in the above method, the administration of the high molecular weight PEG composition (1) reduces the binding of anti-polyethylene glycol antibodies to the at least one pegylated therapeutic composition, and (2) restores the pharmacokinetics of the at least one pegylated therapeutic composition.

In one aspect in the above method, the subject has a high titer of anti-polyethylene glycol antibodies.

In another aspect of the above method, the at least one pegylated therapeutic composition has an improved circulation half-life.

As mentioned above, the high molecular weight PEG composition can be administered to the subject in an amount of from about 1 to about 2500 milligrams per kilogram. Alternatively, the high molecular weight PEG composition can be administered to the subject in an amount of from about 50 to about 2200 milligrams per kilogram. Still further alternatively, the high molecular weight PEG composition can be administered in an amount of 100 to about 2000 milligrams per kilogram.

Any high molecular weight PEG having a molecular weight between about 20 kDa to about 200 kDa can be used in the high molecular weight PEG composition and the above method. In one aspect, the high molecular weight PEG has a molecular weight between about 20 kDa to about 200 kDa. In one aspect, the high molecular weight PEG has a molecular weight between about 20 kDa to about 190 kDa. In one aspect, the high molecular weight PEG has a molecular weight between about 20 kDa to about 180 kDa. In one aspect, the high molecular weight PEG has a molecular weight between about 20 kDa to about 170 kDa. In one aspect, the high molecular weight PEG has a molecular weight between about 20 kDa to about 160 kDa. In one aspect, the high molecular weight PEG has a molecular weight between about 20 kDa to about 150 kDa. In one aspect, the high molecular weight PEG has a molecular weight between about 20 kDa to about 140 kDa. In one aspect, the high molecular weight PEG has a molecular weight between about 20 kDa to about 130 kDa. In one aspect, the high molecular weight PEG has a molecular weight between about 20 kDa to about 120 kDa. In one aspect, the high molecular weight PEG has a molecular weight between about 20 kDa to about 110 kDa. In one aspect, the high molecular weight PEG has a molecular weight between about 20 kDa to about 100 kDa. In one aspect, the high molecular weight PEG has a molecular weight between about 20 kDa to about 90 kDa. In another aspect, the high molecular weight PEG has a molecular weight between about 20 kDa to about 80 kDa. In another aspect, the high molecular weight PEG has a molecular weight between about 20 kDa to about 70 kDa. In another aspect, the high molecular weight PEG has a molecular weight between about 20 kDa to about 60 kDa. In another aspect, the high molecular weight PEG has a molecular weight between about 20 kDa to about 50 kDa. In another aspect, the high molecular weight PEG has a molecular weight between about 20 kDa to about 40 kDa. In yet another aspect, the high molecular weight PEG can have a molecular weight of about 20 kDa, about 25 kDa, about 30 kDa, about 40 kDa, about kDa, about 60 kDa, about 70 kDa, about 75 kDa, about 80 kDa, about 90 kDa, about 100 kDa, about 110 kDa, about 120 kDa, about 130 kDa, about 140 kDa, about 150 kDa, about 160 kDa, about 170 kDa, about 180 kDa, about 190 kDa or about 200 kDa or combinations thereof.

In one aspect, the high molecular weight PEG used in the high molecular weight PEG composition and in the above method can have a geometry that is linear. In another aspect, the high molecular weight PEG can have a geometry that is branched. In yet another aspect, the high molecular weight PEG has a geometry that is star-shaped. In still yet another aspect, the high molecular weight PEG has a geometry that is comb-shaped.

In aspects when the high molecular weight PEG composition is to be administered to the subject prior to the administration of at least one pegylated therapeutic composition, the at least one high molecular weight PEG composition can be administered at least 30 seconds, at least 60 seconds, at least 90 seconds, at least 2 minutes, at least 3 minutes, at least 4 minutes, at least 5 minutes, at least 10 minutes, at least 15 minutes, at least 20 minutes, at least 25 minutes, at least 30 minutes, at least 40 minutes, at least 45 minutes, at least 50 minutes, at least 60 minutes, at least 90 minutes, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours prior to administration of the at least one pegylated therapeutic composition.

Any type of pegylated therapeutic composition can be used in the above method. For example, the at least one pegylated therapeutic composition can comprise at least one protein, peptide, antibody, enzyme, liposome, aptamer, dendrimer, polymeric particle, micelle, inorganic nanoparticle or combinations thereof. In one aspect, the at least one pegylated therapeutic composition comprises a protein. In another aspect, the at least one pegylated therapeutic composition comprises a peptide. In yet another aspect, the at least one pegylated therapeutic composition comprises an antibody (such as a monoclonal antibody, a chimeric antibody, a humanized antibody, a fully human antibody, a bi-specific antibody, a multi-specific antibody, an antibody fragment, or combinations thereof). In another aspect, the at least one pegylated therapeutic composition comprises an enzyme. In still yet another aspect, the at least one pegylated therapeutic comprises a dendrimer. In still yet another aspect, the at least one pegylated therapeutic composition comprises a liposome. In still yet another aspect, the at least one pegylated therapeutic composition comprises a polymeric particle. In still yet another embodiment, the at least one pegylated therapeutic composition comprises a micelle. In still yet another aspect, the at least one pegylated therapeutic composition comprises an inorganic nanoparticle.

In still yet a further aspect, the present disclosure relates to a method of reducing or attenuating the formation of anti-PEG antibodies or a high-titer of anti-PEG antibodies in a subject that is suffering from a disease and in need of treatment or repeated treatment thereof. The method comprises the step of administering from about 1 to about 2500 milligrams per kilogram of at least one high molecular weight polyethylene glycol composition, from about 1 to about 2500 milligrams per kilogram of at least one low molecular weight polyethylene glycol composition or from about 1 to about 2500 milligrams per kilogram of a combination of at least one high molecular weight polyethylene glycol composition and at least one low molecular weight polyethylene glycol composition to a subject either prior to administration of at least one pegylated therapeutic composition (e.g., namely, before the start of treatment of any kind) or that has previously been administered at least one pegylated therapeutic composition (and will receive subsequent treatments with the at least one pegylated therapeutic or an alternative pegylated therapeutic).

The high molecular weight PEG composition, the low molecular weight PEG composition or combination of the high molecular weight PEG composition and low molecular weight PEG composition used in the above method can be administered prior to the administration of the at least one pegylated therapeutic composition (or repeated administration thereof). For example, the high molecular weight PEG composition, the low molecular weight PEG composition or combination of the high molecular weight PEG composition and low molecular weight PEG composition used in the above method can be administered prior to the subject receiving any treatment whatsoever with at least one pegylated therapeutic composition. Alternatively, the high molecular weight PEG composition, the low molecular weight PEG composition or combination of the high molecular weight PEG composition and low molecular weight PEG composition used in the above method can be administered prior to the subject receiving any further or subsequent treatments with at least one pegylated therapeutic composition.

In one aspect, the high molecular weight PEG composition, the low molecular weight PEG composition or combination of the high molecular weight PEG composition and low molecular weight PEG composition can be administered simultaneously with any administration of the at least one pegylated therapeutic composition. For example, in this aspect, the high molecular weight PEG composition, low molecular weight PEG composition or combination of high molecular weight PEG composition and low molecular weight PEG composition can be co-administered with the at least one pegylated therapeutic composition.

As mentioned above, the high molecular weight PEG composition, the low molecular weight PEG composition or combination of the high molecular weight PEG composition and low molecular weight PEG composition can be administered to the subject in an amount of from about 1 to about 2500 milligrams per kilogram. Alternatively, the high molecular weight PEG composition, the low molecular weight PEG composition or combination of the high molecular weight PEG composition and low molecular weight PEG composition can be administered to the subject in an amount of from about 50 to about 2200 milligrams per kilogram. Still further alternatively, the high molecular weight PEG composition, the low molecular weight PEG composition or combination of the high molecular weight PEG composition and low molecular weight PEG composition can be administered in an amount of 100 to about 2000 milligrams per kilogram.

In aspects when the high molecular weight PEG composition, the low molecular weight PEG composition or combination of the high molecular weight PEG composition and low molecular weight PEG composition is to be administered to the subject prior to the administration of at least one pegylated therapeutic composition, the at least one high molecular weight PEG composition can be administered at least 30 seconds, at least 60 seconds, at least 90 seconds, at least 2 minutes, at least 3 minutes, at least 4 minutes, at least 5 minutes, at least 10 minutes, at least 15 minutes, at least 20 minutes, at least 25 minutes, at least 30 minutes, at least 40 minutes, at least 45 minutes, at least 50 minutes, at least 60 minutes, at least 90 minutes, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours prior to administration of the at least one pegylated therapeutic composition.

The above method can be used with any type of pegylated therapeutic composition. For example, the at least one pegylated therapeutic composition can comprise at least one protein, peptide, antibody, enzyme, liposome, aptamer, dendrimer, polymeric particle, micelle, inorganic nanoparticle or combinations thereof. In one aspect, the at least one pegylated therapeutic composition comprises a protein. In another aspect, the at least one pegylated therapeutic composition comprises a peptide. In yet another aspect, the at least one pegylated therapeutic composition comprises an antibody (such as a monoclonal antibody, a chimeric antibody, a humanized antibody, a fully human antibody, a bi-specific antibody, a multi-specific antibody, an antibody fragment, or combinations thereof). In another aspect, the at least one pegylated therapeutic composition comprises an enzyme. In still yet another aspect, the at least one pegylated therapeutic comprises a dendrimer. In still yet another aspect, the at least one pegylated therapeutic composition comprises a liposome. In still yet another aspect, the at least one pegylated therapeutic composition comprises a polymeric particle. In still yet another embodiment, the at least one pegylated therapeutic composition comprises a micelle. In still yet another aspect, the at least one pegylated therapeutic composition comprises an inorganic nanoparticle.

BRIEF DESCRIPTION OF THE DRAWINGS

FIG. 1(A) shows hematoxylin and eosin (H&E) stain of kidney section, FIG. 1(B) shows periodic acid-schiff stain of kidney section and FIG. 1 (C) shows H&E of liver. Tissues were determined by a veterinary pathologist to have no evidence of adverse effects.

FIGS. 2 (C) and (D) are identical to panel B, except with the use of PEG 20 kDa (C) or PEG 40 kDa (D).

FIG. 3 shows pre-treatment with free PEG significantly increases the plasma AUC of PLD in mice and delays hepatic distribution.

FIG. 4(A) shows APA concentrations over time in mice that had previously been vaccinated via the administration of PEGylated liposomes (on day 0) and then were given weekly injections of either PBS or free PEG 40 kDa (550 mg/kg, days 14, 21, 28, and 35). FIG. 4(B) shows APA concentrations over time in mice that had never previously been vaccinated against PEG that were given weekly injections of free PEG 40 kDa (550 mg/kg on days 0, 7, and 14).

FIG. 5(A) shows that mice that had previously been vaccinated against PEG were given a dose of free PEG 40 kDa (550 mg/kg), and arterial blood pressure was monitored continuously for 20 minutes post-injection. FIG. 5(B) shows that in the same experiment as panel A, heart rate was also continuously monitored at the same time.

FIG. 6 shows that the administration of free PEG to sensitized animals does not form immune complexes in the kidney. FIG. 6 shows that mice were vaccinated against PEG via the i.v. administration of PEGylated liposomes, then given either PBS (control) or free PEG 20 kDa (550 mg/kg) weekly for 3 weeks. One week following the final PEG dose, the left kidney was collected, cryosectioned, and IHC-stained for IgG, IgM, C3, and PEG.

FIG. 7 shows the APA concentrations over time in mice that received either PBS, PEG 40 kDa (550 mg/kg), or PEG 40 kDa (55 mg/kg) thirty minutes prior to an injection of empty PEGylated liposomes.

DETAILED DESCRIPTION

Figure 1:
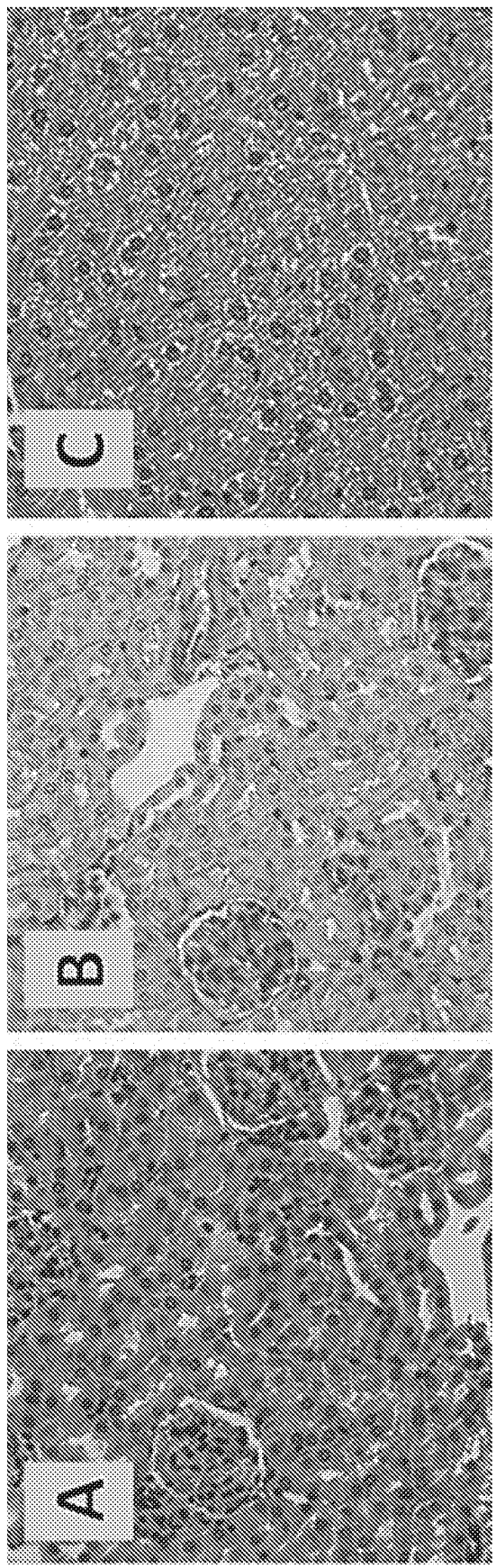
FIG. 1 shows the histology of kidney and liver following exogeneous administration of APA followed by free PEG 20 kDa.

The present disclosure relates to methods for preventing or reducing the detrimental effects that are caused by or result from the presence of anti-PEG antibodies in a subject suffering from a disease and that is about to receive treatment and/or is receiving treatment with at least one pegylated therapeutic composition. Examples of some of the detrimental effects caused by anti-PEG antibodies, particularly in subjects having high titers of such antibodies, include, a reduction in the therapeutic efficacy of the at least one pegylated therapeutic composition (such as by decreasing the elimination half-life of the composition thus causing a reduction in the pharmacokinetic profile (e.g., the $C_{max}$, $T_{max}$ and AUC) of the composition) and/or adverse reactions (such as anaphylaxis). The methods described herein involve administering to a subject in need of treatment or continued treatment thereof an effective amount of at least one high molecular weight polyethylene glycol (PEG) composition. The at least one high molecular weight PEG composition can be administered to the subject prior to or simultaneously with the administration of the at least one pegylated therapeutic composition. As will be discussed in more detail herein, the high molecular weight PEG used in the high molecular weight PEG composition can have a molecular weight between about 20 kDa to about 200 kDa.

Finally, the present disclosure relates to methods of reducing or attenuating the formation of anti-PEG antibodies in a subject suffering from a disease and in need of treatment or continued treatment thereof. The methods described herein involve administering to the subject prior to or during subsequent treatment with at least one pegylated therapeutic composition at least one high molecular weight PEG composition, at least one low molecular weight PEG composition or a combination of at least one high molecular weight PEG composition or at least one low molecular weight PEG composition.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

The term "administered", "administering" or "administration" as used interchangeably herein refers to a mode of delivery, including, without limitation, oral, nasal, pulmonary, transdermal, such as passive or iontophoretic delivery, or parenteral, e.g., rectal, depot, subcutaneous, intravenous, intramuscular, intraperitoneally, intraarterially, intra-cerebella, ophthalmic solution or an ointment. For example, in one aspect, the at least one high molecular weight polyethylene glycol composition can be administered to the subject by direct intramuscular injection. Alternatively, the at least one high molecular weight polyethylene glycol composition can be administered to the subject intravenously. In another aspect, the at least one pegylated therapeutic composition can be administered to the subject by direct intramuscular injection. Alternatively, in another aspect, the at least one pegylated therapeutic composition can be administered to the subject intravenously.

"Anti-polyethylene glycol antibodies" or "anti-PEG antibodies" as used interchangeably herein refers to antibodies which are generated as part of an immune response against the pegylated portion of a pegylated therapeutic composition. Anti-polyethylene glycol antibodies or anti-PEG antibodies may be IgA, IgD, IgE, IgG, IgM or combinations thereof. In one aspect, the anti-polyethylene glycol antibodies or anti-PEG antibodies are IgG or IgM or combinations thereof. In another aspect, the anti-polyethylene glycol antibodies or anti-PEG antibodies are IgG. In still yet another aspect, anti-polyethylene glycol antibodies or anti-PEG antibodies are IgM. The anti-polyethylene glycol antibody or anti-PEG antibody can be any type of antibody known in the art (e.g, such as a polyclonal antibody, monoclonal antibody, a chimeric antibody, a humanized antibody, a fully human antibody, a bi-specific antibody, a multi-specific antibody, an antibody fragment, or combinations thereof). In one aspect, the anti-PEG antibodies are monospecific antibodies (of any isotype such as IgA, IgD, IgE, IgG and/or IgM).

The term "an effective amount" as used herein refers to an amount effective, at dosages, and for periods of time necessary, to achieve the desired result with respect to the treatment of a condition or disease. For example, an amount of at least one high molecular weight PEG composition that reduces the accelerated blood clearance, increases the circulation half-life or restores the pharmacokinetics of at least one pegylated therapeutic composition would be effective. Alternatively, for example, in the treatment of a cancer, at least one pegylated therapeutic composition, which decreases, prevents, delays or suppresses or arrests any symptoms of the cancer would be effective. An effective amount of at least one high molecular weight PEG composition is not required to completely eliminate any anti-PEG antibodies or fully restore the pharmacokinetic profile of at least one pegylated therapeutic composition. Likewise, an effective amount of at least one pegylated therapeutic composition is not required to cure a disease or condition but will provide a treatment for a disease or condition such that the onset of the disease or condition is delayed, hindered or prevented, or the disease or condition symptoms are ameliorated. The effective amount may be divided into one, two or more doses in a suitable form to be administered at one, two or more times throughout a designated time period.

"High molecular weight polyethylene glycol", "high molecular weight PEG" or "high molecular weight free PEG" as used interchangeably herein, refers to a PEG molecule having a molecular weight between about 20 kDa to about 200 kDa. In one aspect, the high molecular weight PEG has a molecular weight between about 20 kDa to about 200 kDa. In one aspect, the high molecular weight PEG has a molecular weight between about 20 kDa to about 190 kDa. In one aspect, the high molecular weight PEG has a molecular weight between about 20 kDa to about 180 kDa. In one aspect, the high molecular weight PEG has a molecular weight between about 20 kDa to about 170 kDa. In one aspect, the high molecular weight PEG has a molecular weight between about 20 kDa to about 160 kDa. In one aspect, the high molecular weight PEG has a molecular weight between about 20 kDa to about 150 kDa. In one aspect, the high molecular weight PEG has a molecular weight between about 20 kDa to about 140 kDa. In one aspect, the high molecular weight PEG has a molecular weight between about 20 kDa to about 130 kDa. In one aspect, the high molecular weight PEG has a molecular weight between about 20 kDa to about 120 kDa. In one aspect, the high molecular weight PEG has a molecular weight between about 20 kDa to about 110 kDa. In one aspect, the high molecular weight PEG has a molecular weight between about 20 kDa to about 100 kDa. In one aspect, the high molecular weight PEG has a molecular weight between about 20 kDa to about 90 kDa. In another aspect, the high molecular weight PEG has a molecular weight between about 20 kDa to about 80 kDa. In another aspect, the high molecular weight PEG has a molecular weight between about 20 kDa to about 70 kDa. In another aspect, the high molecular weight PEG has a molecular weight between about 20 kDa to about 60 kDa. In another aspect, the high molecular weight PEG has a molecular weight between about 20 kDa to about 50 kDa. In another aspect, the high molecular weight PEG has a molecular weight between about 20 kDa to about 40 kDa. In yet another aspect, the high molecular weight PEG can have a molecular weight of about 20 kDa. In yet another aspect, the high molecular weight PEG can have a molecular weight of about 25 kDa. In yet another aspect, the high molecular weight PEG can have a molecular weight of about 30 kDa. In yet another aspect, the high molecular weight PEG can have a molecular weight of about 40 kDa. In yet another aspect, the high molecular weight PEG can have a molecular weight of about 50 kDa. In yet another aspect, the high molecular weight PEG can have a molecular weight of about 60 kDa. In yet another aspect, the high molecular weight PEG can have a molecular weight of about 70 kDa. In yet another aspect, the high molecular weight PEG can have a molecular weight of about 75 kDa. In yet another aspect, the high molecular weight PEG can have a molecular weight of about 80 kDa. In yet another aspect, the high molecular weight PEG can have a molecular weight of about 90 kDa. In yet another aspect, the high molecular weight PEG can have a molecular weight of about 100 kDa. In yet another aspect, the high molecular weight PEG can have a molecular weight of about 110 kDa. In yet another aspect, the high molecular weight PEG can have a molecular weight of about 120 kDa. In yet another aspect, the high molecular weight PEG can have a molecular weight of about 130 kDa. In yet another aspect, the high molecular weight PEG can have a molecular weight of about 140 kDa. In yet another aspect, the high molecular weight PEG can have a molecular weight of about 150 kDa. In yet another aspect, the high molecular weight PEG can have a molecular weight of about 160 kDa. In yet another aspect, the high molecular weight PEG can have a molecular weight of about 170 kDa. In yet another aspect, the high molecular weight PEG can have a molecular weight of about 180 kDa. In yet another aspect, the high molecular weight PEG can have a molecular weight of about 190 kDa. In yet another aspect, the high molecular weight PEG can have a molecular weight of about 200 kDa. In yet a further aspect, if more than one high molecular weight PEG is to be used in the methods herein, any combinations of the above described high molecular weight PEGs can be used.

Any high molecular weight PEG can be used in the methods of the present disclosure. Such high molecular weight PEGs can be obtained from commercially available sources such as from Sigma-Aldrich (St. Louis, MO), Advanced Biochemicals (Lawrenceville, GA) or Broad-Pharm (San Diego, CA). Alternatively, such high molecular weight PEGs for use in the methods of the present disclosure can be synthetized using routine techniques known in the art such as those described in: Herzberger, J., et al., Polymerization of Ethylene Oxide, Propylene Oxide, and Other Alkylene Oxides: Synthesis, Novel Polymer Architectures, and Bioconjugation. Chemical Reviews, 2016. 116(4): p. 2170-2243., or Vivaldo-Lima, E., et al., An Updated Review on Suspension Polymerization. Industrial & Engineering Chemistry Research, 1997. 36(4): p. 939-965.

"High molecular weight polyethylene glycol composition" or "high molecular weight PEG composition" as used herein refers to a composition comprising a high molecular weight PEG and optionally, one or more pharmaceutically acceptable excipients (such as for example, buffers (e.g., mannitol, sorbitol, and glycerol), diluents, carriers or combinations thereof.

"Low molecular weight polyethylene glycol", "low molecular weight PEG" or "low molecular weight free PEG" as used interchangeably herein, refers to a PEG molecule having a molecular weight between less than about 20 kDa. In one aspect, the low molecular weight PEG has a molecular weight between about 200 Da to about 19 kDa. In another aspect, the low molecular weight PEG has a molecular weight between about 200 Da to about 18 kDa. In another aspect, the low molecular weight PEG has a molecular weight between about 200 Da to about 17 kDa. In another aspect, the low molecular weight PEG has a molecular weight between about 200 Da to about 16 kDa. In another aspect, the low molecular weight PEG has a molecular weight between about 200 Da to about 15 kDa. In another aspect, the low molecular weight PEG has a molecular weight between about 200 Da to about 14 kDa. In another aspect, the low molecular weight PEG has a molecular weight between about 200 Da to about 13 kDa. In another aspect, the low molecular weight PEG has a molecular weight between about 200 Da to about 12 kDa. In another aspect, the low molecular weight PEG has a molecular weight between about 200 Da to about 11 kDa. In another aspect, the low molecular weight PEG has a molecular weight between about 200 Da to about 10 kDa. In another aspect, the low molecular weight PEG has a molecular weight between about 200 Da to about 9 kDa. In another aspect, the low molecular weight PEG has a molecular weight between about 200 Da to about 8 kDa. In another aspect, the low molecular weight PEG has a molecular weight between about 200 Da to about 7 kDa. In another aspect, the low molecular weight PEG has a molecular weight between about 200 Da to about 6 kDa. In another aspect, the low molecular weight PEG has a molecular weight between about 200 Da to about 5 kDa. In another aspect, the low molecular weight PEG has a molecular weight between about 200 Da to about 4 kDa. In another aspect, the low molecular weight PEG has a molecular weight between about 200 Da to about 3 kDa. In another aspect, the low molecular weight PEG has a molecular weight between about 200 Da to about 2 kDa. In another aspect, the low molecular weight PEG has a molecular weight between about 200 Da to about 1 kDa. In yet another aspect, the low molecular weight PEG has a molecular weight of about 19 kDa. In yet another aspect, the low molecular weight PEG has a molecular weight of about 18 kDa. In yet another aspect, the low molecular weight PEG has a molecular weight of about 17 kDa. In yet another aspect, the low molecular weight PEG has a molecular weight of about 16 kDa. In yet another aspect, the low molecular weight PEG has a molecular weight of about 15 kDa. In yet another aspect, the low molecular weight PEG has a molecular weight of about 14 kDa. In yet another aspect, the low molecular weight PEG has a molecular weight of about 13 kDa. In yet another aspect, the low molecular weight PEG has a molecular weight of about 12 kDa. In yet another aspect, the low molecular weight PEG has a molecular weight of about 11 kDa. In yet another aspect, the low molecular weight PEG has a molecular weight of about 10 kDa. In yet another aspect, the low molecular weight PEG has a molecular weight of about 9 kDa. In yet another aspect, the low molecular weight PEG has a molecular weight of about 8 kDa. In yet another aspect, the low molecular weight PEG has a molecular weight of about 7 kDa. In yet another aspect, the low molecular weight PEG has a molecular weight of about 6 kDa. In yet another aspect, the low molecular weight PEG has a molecular weight of about 5 kDa. In yet another aspect, the low molecular weight PEG has a molecular weight of about 4 kDa. In yet another aspect, the low molecular weight PEG has a molecular weight of about 3 kDa. In yet another aspect, the low molecular weight PEG has a molecular weight of about 2 kDa. In yet another aspect, the low molecular weight PEG has a molecular weight of about 1 kDa. In yet another aspect, the low molecular weight PEG has a molecular weight of about 900 Da. In yet another aspect, the low molecular weight PEG has a molecular weight of about 800 Da. In yet another aspect, the low molecular weight PEG has a molecular weight of about 700 Da. In yet another aspect, the low molecular weight PEG has a molecular weight of about 600 Da. In yet another aspect, the low molecular weight PEG has a molecular weight of about 500 Da. In yet another aspect, the low molecular weight PEG has a molecular weight of about 400 Da. In yet another aspect, the low molecular weight PEG has a molecular weight of about 300 Da. In yet another aspect, the low molecular weight PEG has a molecular weight of about 200 Da.

Any low molecular weight PEG can be used in the methods of the present disclosure. Such high molecular weight PEGs can be obtained from commercially available sources such as from Sigma-Aldrich (St. Louis, MO), Advanced Biochemicals (Lawrenceville, GA) or Broad-Pharm (San Diego, CA). Alternatively, such low molecular weight PEGs for use in the methods of the present disclosure can be synthetized using routine techniques known in the art such as those described in: Herzberger, J., et al., Polymerization of Ethylene Oxide, Propylene Oxide, and Other Alkylene Oxides: Synthesis, Novel Polymer Architectures, and Bioconjugation. Chemical Reviews, 2016. 116(4): p. 2170-2243., or Vivaldo-Lima, E., et al., An Updated Review on Suspension Polymerization. Industrial & Engineering Chemistry Research, 1997. 36(4): p. 939-965.

"Low molecular weight polyethylene glycol composition" or "low molecular weight PEG composition" as used herein refers to a composition comprising a low molecular weight PEG and optionally, one or more pharmaceutically acceptable excipients (such as for example, buffers (e.g., mannitol, sorbitol, and glycerol), diluents, carriers or combinations thereof.

"Pegylated or PEGylated therapeutic" as used herein refers to molecules, compounds and/or medicines, in which one or more polyethylene glycol molecules are attached thereto. Examples of pegylated therapeutics include proteins, peptides, antibodies (such as a monoclonal antibody, a chimeric antibody, a humanized antibody, a fully human antibody, a bi-specific antibody, a multi-specific antibody, an antibody fragment or combinations thereof), enzymes, liposomes, aptamers, dendrimers, polymeric particles, micelles, inorganic nanoparticles or any combinations thereof. In one aspect, the pegylated therapeutic is a protein. In another aspect, the pegylated therapeutic is a peptide. In yet another aspect, the pegylated therapeutic is an antibody. In still yet another aspect, the pegylated therapeutic is an enzyme. In still yet another aspect, the pegylated therapeutic is a liposome. In still yet another aspect, the pegylated therapeutic is an aptamer. In still yet another aspect, the pegylated therapeutic is a dendrimer. In still yet another aspect, the pegylated therapeutic is a polymeric particle. In still yet another aspect, the pegylated therapeutic is micelle. In still yet another aspect, the pegylated therapeutic is an inorganic nanoparticle.

The methods of the above disclosure can be used in connection or conjunction with any pegylated therapeutic that causes the production of anti-PEG antibodies or is negatively affected by the presence of anti-PEG antibodies. Methods for making pegylated therapeutics are well known in the art (see Turecek, P. L., et al., PEGylation of Biopharmaceuticals: A Review of Chemistry and Nonclinical Safety Information of Approved Drugs. J Pharm Sci, 2016. 105(2): p. 460-475, or Jevsevar, S., M. Kunstelj, and V.G. Porekar, PEGylation of therapeutic proteins. Biotechnol J, 2010. 5(1): p. 113-28.)

Examples of some pegylated therapeutics that can be used in the methods of the present disclosure include pegadamase, pegaspargase, pegvisomant, pegloticase, PEG-interferon alpha 2b, pegfilgrastim, PEG-EPO, peginesatide, pegaptanib, PEG-interferon alpha 2a, certolizumab, peginterferon beta-1, PEGylated liposomal doxorubicin, pegvalia, se, PEGylated Factor VIII, naloxegol, nonacog beta pegol, PEGylated liposomal irinotecan, turoctocog alfa pegol (truncated factor VIII with PEG 40 kDa), PEGylated B-domain truncated factor VIII, PEGylated liposomal cisplatin, PEGylated liposomal camptothecin analog, elapegademase, PEG-somatropin, Polyethylene glycol loxenatide, 18F-PEG6-IPQA radiotracer, PEG-treated IVIG, PEGylated arginine deaminase, Pyridoxalated hemoglobin polyoxyethylene conjugate (PHP), Peginterferon alfa 2b 48kDA, PEG-Darbepoetin, TransCon PEG treprostinil, pegylated interferon-lambda, Etirinotecan Pegol, PEGylated recombinant human hyaluronidase, Dapirolizumab Pegol, PEG-liposomal prednisolone sodium phosphate, PEGylated GLP-1 agonist, calaspargase pegol, PEG-glucocerbrosidase, Nanoliposomal vinorelbine/Vinorelbine encapsulate liposome, pegnivacogin, PEGylated liposomal cisplatin, PEGylated basal insulin, PEGylated IL-2 or combinations thereof.

"Pegylated therapeutic composition" as used herein refers to a composition comprising a pegylated therapeutic and optionally, one or more pharmaceutically acceptable excipients (such as for example, buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol), diluents, carriers or combinations thereof.

"Polyethylene glycol(s)" or "PEG" as used interchangeably herein refer to amphiphilic and relatively chemically inert polymers comprising repetitive or repeating units of ethylene oxide. PEGs have various configurations or geometries, such as linear, branched, star-shaped or comb-shaped. In one aspect, the PEG used in the methods described herein has a linear configuration or geometry. In another aspect, the PEG used in the methods described herein has a branched configuration or geometry. In yet another aspect, the PEG used in the methods described herein has a star-shaped configuration or geometry. In still yet another aspect, the PEG used in the methods described herein has a comb-shaped configuration or geometry. In another aspect, the PEG used in the methods described herein have a linear or branched shaped configuration or geometry. In still yet another aspect, the PEG used in the methods described herein has a linear, branched or star-shaped configuration or geometry. In still yet another aspect, the PEG used in the methods described herein has a linear, branched, star-shaped or comb-shaped configuration or geometry. In still yet another aspect, several different PEGs can be used in the methods described herein which may have a combination of linear, branched, star-shaped or comb-shaped configurations or geometries.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In one aspect, the subject is a human. In another aspect, the subject is a human who has been determined to have or possess a high titer of anti-PEG antibodies. As used herein, the phrase "high titer of anti-PEG antibodies" refers to a subject (e.g., human) (a) who is non-responsive or exhibits a poor response (e.g., namely a subject who is non-responsive to therapy or who exhibits less clinical response than anticipated by a treating physician when treating the subject with at least one pegylated therapeutic composition) to at least one pegylated therapeutic composition; (b) who, after obtaining and testing a biological sample (such as a whole blood sample, serum, plasma, etc.) from that subject (using routine techniques known in the art), is determined to have at least a detectable level of anti-PEG antibodies; or (c) a combination of (a) and (b). For example, a subject having a high titer of anti-PEG antibodies may have anti-PEG antibodies detected in an amount of at least about 1 ug/mL or greater. For example, a high titer of anti-PEG antibodies may be about 1 ug/mL or greater, about 1.25 ug/mL or greater, about 1.50 ug/mL or greater, about 1.75 ug/mL or greater, about 2.0 or greater, etc.

The term "treat," "treating" or "treatment" are each used interchangeably herein to describe obtaining a desired pharmacological and/or physiologic effect, e.g., inhibiting cancer growth, or ameliorating ischemic injury to an organ (e.g., heart). The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition (e.g., cancer, leukemia, rheumatoid arthritis, ulcerative colitis, Crohn's disease, asthma, COPD, ischemia disease, etc.) from occurring in an individual who may be pre-disposed to the disease but has not yet been diagnosed as having it; (2) inhibiting a disease (e.g., by arresting its development); or (3) relieving a disease (e.g., reducing symptoms associated with the disease).

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

Methods of the Reducing Accelerated Blood Clearance

In one aspect, the present disclosure relates to methods of reducing the accelerated blood clearance (ABC) of at least one pegylated therapeutic composition resulting from the presence of one or more anti-PEG antibodies in a subject that is suffering from a disease and in need of treatment or continued treatment thereof. Specifically, the method involves administering to the subject in need of treatment and/or continued treatment, an effective amount of at least one high molecular weight PEG composition at an appropriate period or time point(s) prior to and/or during the course of treatment. While not wishing to be bound by any theory, it is believed that the administration of one or more high molecular weight PEG compositions saturates at least some or a certain percentage of the circulating anti-PEG antibodies and B-cell receptors on anti-PEG B cells in the subject thereby preventing, (competitively) inhibiting and/or interfering with their binding and/or interaction with the one or more pegylated therapeutic compositions. Such interference can reduce the negative effects of anti-PEG antibodies in the subject who is to receive treatment or continued treatment.

In one aspect, the subject being treated pursuant to the method described herein has not yet been administered the at least one pegylated therapeutic composition for treatment of the disease. Under such a circumstance, the subject may be administered at least one high molecular weight PEG composition prophylactically, in advance of treatment, to assist in reducing and/or preventing ABC once the pegylated therapeutic composition is administered. For example, the treating physician may know or may have determined (using routine techniques known in the art) that the subject has a high-titer of circulating anti-PEG antibodies or pre-existing circulating anti-PEG antibodies (prior to beginning the treatment). Alternatively, the circulating anti-PEG antibody titer level of the subject may not be known or may not have been determined.

In still yet a further aspect, the high molecular weight PEG composition can be administered to the subject simultaneously with the administration of the at least one pegylated therapeutic composition. For example, the at least one high molecular weight PEG composition can be co-administered with the at least one pegylated therapeutic composition. For example, the at least one high molecular weight PEG may be included as part of the composition comprising the pegylated therapeutic such that both the high molecular weight PEG and pegylated therapeutic are administered together as a single formulation or composition. Such a formulation or composition can be prepared using routine techniques known in the art.

As mentioned previously, the methods of the present disclosure involve administering an effective amount of at least one high molecular weight PEG composition to a subject suffering from a disease and in need of treatment and/or continued treatment thereof. Methods for determining an effective amount of at least one high molecular weight PEG composition to administer to the subject can be determined by the treating physician using routine techniques known in the art. For example, an effective amount of the at least one high molecular weight PEG can be from about 0.1 to about 500 milligrams per kilogram of the subject. Alternatively, the effective amount can be from about 0.5 to about 400 milligrams per kilogram of the subject. Alternatively, the effective amount can be from about 0.75 to about 300 milligrams per kilogram of the subject. Still further alternatively, the effective amount can be from about 1.0 to about 250 milligrams per kilogram of the subject. Still further alternatively, the effective amount can be from about 5.0 to about 200 milligrams per kilogram of the subject. Still further alternatively, the effective amount can be from about 10 to about 200 milligrams per kilogram of the subject. Still further alternatively, the effective amount can be from about 5 to about 150 milligrams per kilogram of the subject. Alternatively, the effective amount can be from about 10 to about 150 milligrams per kilogram of the subject. Alternatively, the effective amount can be from about 5 to about 100 milligrams per kilogram of the subject. Alternatively, the effective amount can be from about 10 to about 100 milligrams per kilogram of the subject.

In aspects when the high molecular weight PEG is to be administered to the subject prior to the administration of at least one pegylated therapeutic composition, then at least one high molecular weight PEG composition can be administered at least 5 seconds, at least 10 seconds, at least 15 seconds, at least 20 seconds, at least 30 seconds, at least 60 seconds, at least 90 seconds, at least 2 minutes, at least 3 minutes, at least 4 minutes, at least 5 minutes, at least 10 minutes, at least minutes, at least 20 minutes, at least 25 minutes, at least 30 minutes, at least 40 minutes, at least minutes, at least 50 minutes, at least 60 minutes, at least 90 minutes, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours prior to administration of the at least one pegylated therapeutic composition. In one aspect, the at least one high molecular weight PEG composition can be administered at least 5 seconds prior to administration of the at least one pegylated therapeutic composition. In another aspect, the at least one high molecular weight PEG composition can be administered at least 10 seconds prior to administration of the at least one pegylated therapeutic composition. In yet another aspect, the at least one high molecular weight PEG composition can be administered at least 15 seconds prior to administration of the at least one pegylated therapeutic composition. In yet another aspect, the at least one high molecular weight PEG composition can be administered at least 20 seconds prior to administration of the at least one pegylated therapeutic composition. In yet another aspect, the at least one high molecular weight PEG composition can be administered at least 30 seconds prior to administration of the at least one pegylated therapeutic composition. In yet another aspect, the at least one high molecular weight PEG composition can be administered at least 60 seconds prior to administration of the at least one pegylated therapeutic composition. In yet another aspect, the at least one high molecular weight PEG composition can be administered at least 90 seconds prior to administration of the at least one pegylated therapeutic composition. In yet another aspect, the at least one high molecular weight PEG composition can be administered at least 2 minutes, prior to administration of the at least one pegylated therapeutic composition. In yet another aspect, the at least one high molecular weight PEG composition can be administered at least 3 minutes, prior to administration of the at least one pegylated therapeutic composition. In yet another aspect, the at least one high molecular weight PEG composition can be administered at least 3 minutes, prior to administration of the at least one pegylated therapeutic composition. In yet another aspect, the at least one high molecular weight PEG composition can be administered at least 4 minutes, prior to administration of the at least one pegylated therapeutic composition. In yet another aspect, the at least one high molecular weight PEG composition can be administered at least 5 minutes, prior to administration of the at least one pegylated therapeutic composition. In yet another aspect, the at least one high molecular weight PEG composition can be administered at least 10 minutes, prior to administration of the at least one pegylated therapeutic composition. In yet another aspect, the at least one high molecular weight PEG composition can be administered at least 15 minutes, prior to administration of the at least one pegylated therapeutic composition. In yet another aspect, the at least one high molecular weight PEG composition can be administered at least 20 minutes, prior to administration of the at least one pegylated therapeutic composition. In yet another aspect, the at least one high molecular weight PEG composition can be administered at least 25 minutes, prior to administration of the at least one pegylated therapeutic composition. In yet another aspect, the at least one high molecular weight PEG composition can be administered at least 30 minutes, prior to administration of the at least one pegylated therapeutic composition. In yet another aspect, the at least one high molecular weight PEG composition can be administered at least 40 minutes, prior to administration of the at least one pegylated therapeutic composition. In yet another aspect, the at least one high molecular weight PEG composition can be administered at least 45 minutes, prior to administration of the at least one pegylated therapeutic composition. In yet another aspect, the at least one high molecular weight PEG composition can be administered at least 50 minutes, prior to administration of the at least one pegylated therapeutic composition. In yet another aspect, the at least one high molecular weight PEG composition can be administered at least 60 minutes, prior to administration of the at least one pegylated therapeutic composition. In yet another aspect, the at least one high molecular weight PEG composition can be administered at least 90 minutes, prior to administration of the at least one pegylated therapeutic composition. In yet another aspect, the at least one high molecular weight PEG composition can be administered at least 2 hours, prior to administration of the at least one pegylated therapeutic composition. In yet another aspect, the at least one high molecular weight PEG composition can be administered at least 3 hours, prior to administration of the at least one pegylated therapeutic composition. In yet another aspect, the at least one high molecular weight PEG composition can be administered at least 4 hours, prior to administration of the at least one pegylated therapeutic composition. In yet another aspect, the at least one high molecular weight PEG composition can be administered at least 5 hours, prior to administration of the at least one pegylated therapeutic composition. In yet another aspect, the at least one high molecular weight PEG composition can be administered at least 6 hours, prior to administration of the at least one pegylated therapeutic composition. In yet another aspect, the at least one high molecular weight PEG composition can be administered at least 7 hours, prior to administration of the at least one pegylated therapeutic composition. In yet another aspect, the at least one high molecular weight PEG composition can be administered at least 8 hours, prior to administration of the at least one pegylated therapeutic composition. In yet another aspect, the at least one high molecular weight PEG composition can be administered at least 9 hours, prior to administration of the at least one pegylated therapeutic composition. In yet another aspect, the at least one high molecular weight PEG composition can be administered at least 10 hours, prior to administration of the at least one pegylated therapeutic composition. In yet another aspect, the at least one high molecular weight PEG composition can be administered at least 11 hours, prior to administration of the at least one pegylated therapeutic composition. In yet another aspect, the at least one high molecular weight PEG composition can be administered at least 12 hours, prior to administration of the at least one pegylated therapeutic composition. In yet another aspect, the at least one high molecular weight PEG composition can be administered at least 13 hours, prior to administration of the at least one pegylated therapeutic composition. In yet another aspect, the at least one high molecular weight PEG composition can be administered at least 14 hours, prior to administration of the at least one pegylated therapeutic composition. In yet another aspect, the at least one high molecular weight PEG composition can be administered at least 15 hours, prior to administration of the at least one pegylated therapeutic composition. In yet another aspect, the at least one high molecular weight PEG composition can be administered at least 16 hours, prior to administration of the at least one pegylated therapeutic composition. In yet another aspect, the at least one high molecular weight PEG composition can be administered at least 17 hours, prior to administration of the at least one pegylated therapeutic composition. In yet another aspect, the at least one high molecular weight PEG composition can be administered at least 18 hours, prior to administration of the at least one pegylated therapeutic composition. In yet another aspect, the at least one high molecular weight PEG composition can be administered at least 19 hours, prior to administration of the at least one pegylated therapeutic composition. In yet another aspect, the at least one high molecular weight PEG composition can be administered at least 20 hours, prior to administration of the at least one pegylated therapeutic composition. In yet another aspect, the at least one high molecular weight PEG composition can be administered at least 21 hours, prior to administration of the at least one pegylated therapeutic composition. In yet another aspect, the at least one high molecular weight PEG composition can be administered at least 22 hours, prior to administration of the at least one pegylated therapeutic composition. In yet another aspect, the at least one high molecular weight PEG composition can be administered at least 23 hours, prior to administration of the at least one pegylated therapeutic composition. In yet another aspect, the at least one high molecular weight PEG composition can be administered at least 24 hours, prior to administration of the at least one pegylated therapeutic composition.

The disease in need of treatment thereof is not critical. For example, the disease could be any type, kind, form and/or stage of cancer, rheumatoid arthritis, ulcerative colitis, Crohn's disease, asthma, COPD, diabetes, ischemia disease, renal disease, kidney disease, gout, etc. In one aspect, the disease is cancer. Examples of cancers include breast cancer, cervical cancer, ovary cancer, endometrial cancer, melanoma, uveal melanoma, brain tumor, lung cancer, liver cancer, lymphoma, neuroepithelioma, kidney cancer, bladder cancer, pancreatic cancer, prostate cancer, stomach cancer, colon cancer, uterus cancer, hematopoietic tumors of lymphoid lineage, myeloid leukemia, thyroid cancer, thyroid follicular cancer, myelodysplastic syndrome (MDS), tumor of mesenchymal origin, teratcarcinoma, neuroblastoma, glioma, glioblastoma, keratoacanthomas, analplastic large cell lymphoma, esophageal squamous cell carcinoma, follicular dentritic cell carcinoma, intestinal cancer, muscle invasive cancer, seminal vesicle tumor, epidermal carcinoma, spleen cancer, head and neck cancer, stomach cancer, bone cancer, cancer of retina, biliary cancer, small bowel cancer, salivary gland cancer, uterine sarcoma, cancer of testicles, cancer of connective tissue, prostatic hypertrophy, myelodysplasia, Waldenstrom's macroglobulinemia, nasopharyngeal, neuroendocrine cancer, mesothelioma, angiosarcoma, Kaposi's sarcoma, oesophagogastric, fallopian tube cancer, peritoneal cancer, papillary serous mullerian cancer, malignant ascites, gastrointestinal stromal tumor (GIST), Li-Fraumeni syndrome or Von Hippel-Lindau syndrome (VHL). The hematopoietic tumors of lymphoid lineage may be any of leukemia, acute lymphocytic leukemia, chronic lymphocytic leukemia, B-cell lymphoma, Burkitt's lymphoma, multiple myeloma, Hodgkin's lymphoma, or Non-Hodgkin's lymphoma. The myeloid leukemia may be acute myelogenous leukemia (AML) or chronic myelogenous leukemia (CML). A tumor of mesenchymal origin can include fibrosarcomas or rhabdomyosarcomas.

As mentioned previously herein, the methods of the present disclosure reduce the accelerated blood clearance (ABC) of at least one pegylated therapeutic composition. In one aspect, a treating physician may notice that the effect of at least one pegylated therapeutic composition has dropped off. For example, in the case of pegloticase, a physician might notice that a patient's uric acid plasma concentration begins to rise again just a few days after drug administration. The same is generally true for other pegylated drugs, their presence in a subject's body may be determined via a functional assay, using the drug's activity as an indicator of concentration or also by direct measurement of anti-PEG antibodies in a biological sample (such as whole blood, serum, plasma, etc.).

Additionally, the at least one high molecular weight PEG composition can be administered to the subject as frequently or infrequently as needed as determined by the treating physician based on the reduction and/or continued reduction of ABC of the at least one pegylated therapeutic composition. The treating physician can monitor the ABC of the at least one pegylated therapeutic composition during the course of treatment using routine techniques known in the art and make any clinical adjustments as necessary.

Methods of Increasing the Circulation Half-Life of at Least One Pegylated Therapeutic Composition In another aspect, the present disclosure relates to methods of improving and/or increasing the circulation or circulating half-life of at least one pegylated therapeutic composition that will, has been or will continue to be administered (or repeatedly administered) to a subject that is suffering from a disease and in need of treatment or continued treatment thereof. Specifically, the method involves administering to the subject in need of treatment or continued treatment, an effective amount of at least one high molecular weight PEG composition at an appropriate period or time point(s) prior to and/or during the course of treatment. While not wishing to be bound by any theory, it is believed that the administration of one or more high molecular weight PEG compositions saturates at least some or a certain percentage of the circulating anti-PEG antibodies in the subject thereby preventing, inhibiting and/or interfering with their (competitive) binding and/or interaction with the one or more pegylated therapeutic compositions.

In one aspect, the subject being treated pursuant to the method described herein has not yet been administered at least one pegylated therapeutic composition for treatment of the disease. Under such a circumstance, the subject may be administered at least one high molecular weight PEG composition prophylactically, in advance of treatment, to assist in improving and/or increasing the circulation or circulating half-life of the at least one pegylated therapeutic composition once the composition is ultimately administered to the subject. For example, the treating physician may know or may have determined (using routine techniques known in the art) that the subject has a high-titer of circulating anti-PEG antibodies or pre-existing circulating anti-PEG antibodies (prior to beginning the treatment). Alternatively, the circulating anti-PEG antibody titer level of the subject may not be known or may not have been determined.

In another aspect, the subject being treated pursuant to the method described herein may have been receiving treatment with a specific pegylated therapeutic composition (a "first" pegylated therapeutic composition) and is being switched to a second pegylated therapeutic composition (a "second" pegylated therapeutic composition). In such circumstances, the subject can be administered an effective amount of the at least one high molecular weight PEG composition between administration of the first and second pegylated therapeutic compositions.

Still a further aspect, the subject being treated pursuant to the method described herein may have previously received one or more administrations of the at least one pegylated therapeutic composition. Said another way, the subject is receiving repeated administrations of the at least one pegylated therapeutic composition. Under such a circumstance, the at least one high molecular weight PEG composition is administered to the subject prior to any subsequent or further administration of any (additional) pegylated therapeutic compositions in order to aid in improving and/or increasing the circulating half-life of the pegylated therapeutic composition, particularly in instances where the circulating half-life of the pegylated therapeutic composition has been determined (using routine techniques known in the art) to have been reduced thus impacting the pharmacokinetic profile and/or the efficacy of the pegylated therapeutic composition to treat the disease. The at least one high molecular PEG composition can be administered at any period or time point(s) prior to any subsequent or further administration of the at least one pegylated therapeutic composition. Alternatively, the high molecular weight PEG composition can be administered to the subject simultaneously with the administration of the at least one pegylated therapeutic composition. For example, the at least one high molecular weight PEG composition can be co-administered with the at least one pegylated therapeutic composition. For example, the at least one high molecular weight PEG may be included as part of the composition comprising the pegylated therapeutic such that both the high molecular weight PEG and pegylated therapeutic are administered together as a single formulation or composition. Such a formulation or composition can be prepared using routine techniques known in the art.

As mentioned previously, the method of the present disclosure involves administering an effective amount of at least one high molecular weight PEG composition to a subject suffering from a disease and in need of treatment or continued treatment thereof. Methods for determining an effective amount of at least one high molecular weight PEG composition to administer to the subject can be determined by the treating physician using routine techniques known in the art (such as, for example, performing an assay to measure the level of anti-PEG antibodies). For example, an effective amount of the at least one high molecular weight PEG can be from about 1 to about 2500 milligrams per kilogram of the subject. Alternatively, 10 to about 2500 milligrams per kilogram of the subject. Alternatively, 25 to about 2500 milligrams per kilogram of the subject. Still further alternatively, the effective amount can be from about 50 to about 2500 milligrams per kilogram of the subject. Still further alternatively, the effective amount can be from about 100 to about 2500 milligrams per kilogram of the subject. Still further alternatively, the effective amount can be from about 1 to about 2200 milligrams per kilogram of the subject. Still further alternatively, the effective amount can be from about 10 to about 2200 milligrams per kilogram of the subject. Still further alternatively, the effective amount can be from about 25 to about 2200 milligrams per kilogram of the subject. Still further alternatively, the effective amount can be from about 50 to about 2200 milligrams per kilogram of the subject. Still further alternatively, the effective amount can be from about 100 to about 2200 milligrams per kilogram of the subject. Still further alternatively, the effective amount can be from about 1 to about 2000 milligrams per kilogram of the subject. Still further alternatively, the effective amount can be from about 10 to about 2000 milligrams per kilogram of the subject. Still further alternatively, the effective amount can be from about 25 to about 2000 milligrams per kilogram of the subject. Still further alternatively, the effective amount can be from about 50 to about 2000 milligrams per kilogram of the subject. Still further alternatively, the effective amount can be from about 100 to about 2000 milligrams per kilogram of the subject. Still further alternatively, the effective amount can be from about 1 to about 1500 milligrams per kilogram of the subject. Still further alternatively, the effective amount can be from about 10 to about 1500 milligrams per kilogram of the subject. Still further alternatively, the effective amount can be from about 25 to about 1500 milligrams per kilogram of the subject. Still further alternatively, the effective amount can be from about 50 to about 1500 milligrams per kilogram of the subject. Still further alternatively, the effective amount can be from about 100 to about 1500 milligrams per kilogram of the subject. Still further alternatively, the effective amount can be from about 1 to about 1000 milligrams per kilogram of the subject. Still further alternatively, the effective amount can be from about 10 to about 1000 milligrams per kilogram of the subject. Still further alternatively, the effective amount can be from about 25 to about 1000 milligrams per kilogram of the subject. Still further alternatively, the effective amount can be from about 50 to about 1000 milligrams per kilogram of the subject. Still further alternatively, the effective amount can be from about 100 to about 1000 milligrams per kilogram of the subject. Still further alternatively, the effective amount can be from about 1 to about 750 milligrams per kilogram of the subject. Still further alternatively, the effective amount can be from about 10 to about 750 milligrams per kilogram of the subject. Still further alternatively, the effective amount can be from about 25 to about 750 milligrams per kilogram of the subject. Still further alternatively, the effective amount can be from about 50 to about 750 milligrams per kilogram of the subject. Still further alternatively, the effective amount can be from about 100 to about 750 milligrams per kilogram of the subject. Still further alternatively, the effective amount can be from about 1 to about 500 milligrams per kilogram of the subject. Still further alternatively, the effective amount can be from about 10 to about 500 milligrams per kilogram of the subject. Still further alternatively, the effective amount can be from about 25 to about 500 milligrams per kilogram of the subject. Still further alternatively, the effective amount can be from about 50 to about 500 milligrams per kilogram of the subject. Still further alternatively, the effective amount can be from about 100 to about 500 milligrams per kilogram of the subject.

In aspects when the high molecular weight PEG composition is to be administered to the subject prior to the administration of at least one pegylated therapeutic composition (regardless of whether the at least one pegylated therapeutic composition has not yet been administered previously to the subject and/or if the administration of the at least one pegylated therapeutic composition is subsequent or further to a previous administration(s) of the at least one pegylated therapeutic composition), then at least one high molecular weight PEG composition can be administered at least 5 seconds, at least 10 seconds, at least 15 seconds, at least 20 seconds, at least 30 seconds, at least 60 seconds, at least 90 seconds, at least 2 minutes, at least 3 minutes, at least 4 minutes, at least 5 minutes, at least 10 minutes, at least 15 minutes, at least 20 minutes, at least 25 minutes, at least 30 minutes, at least 40 minutes, at least 45 minutes, at least 50 minutes, at least 60 minutes, at least 90 minutes, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours prior to administration of the at least one pegylated therapeutic composition. In one aspect, the at least one high molecular weight PEG composition can be administered at least 5 seconds prior to administration of the at least one pegylated therapeutic composition. In another aspect, the at least one high molecular weight PEG composition can be administered at least 5 seconds prior to administration of the at least one pegylated therapeutic composition. In yet another aspect, the at least one high molecular weight PEG composition can be administered at least 10 seconds prior to administration of the at least one pegylated therapeutic composition. In yet another aspect, the at least one high molecular weight PEG composition can be administered at least 15 seconds prior to administration of the at least one pegylated therapeutic composition. In yet another aspect, the at least one high molecular weight PEG composition can be administered at least 20 seconds prior to administration of the at least one pegylated therapeutic composition. In yet another aspect, the at least one high molecular weight PEG composition can be administered at least 30 seconds prior to administration of the at least one pegylated therapeutic composition. In yet another aspect, the at least one high molecular weight PEG composition can be administered at least 60 seconds prior to administration of the at least one pegylated therapeutic composition. In yet another aspect, the at least one high molecular weight PEG composition can be administered at least 90 seconds prior to administration of the at least one pegylated therapeutic composition. In yet another aspect, the at least one high molecular weight PEG composition can be administered at least 2 minutes, prior to administration of the at least one pegylated therapeutic composition. In yet another aspect, the at least one high molecular weight PEG composition can be administered at least 3 minutes, prior to administration of the at least one pegylated therapeutic composition. In yet another aspect, the at least one high molecular weight PEG composition can be administered at least 3 minutes, prior to administration of the at least one pegylated therapeutic composition. In yet another aspect, the at least one high molecular weight PEG composition can be administered at least 4 minutes, prior to administration of the at least one pegylated therapeutic composition. In yet another aspect, the at least one high molecular weight PEG composition can be administered at least 5 minutes, prior to administration of the at least one pegylated therapeutic composition. In yet another aspect, the at least one high molecular weight PEG composition can be administered at least 10 minutes, prior to administration of the at least one pegylated therapeutic composition. In yet another aspect, the at least one high molecular weight PEG composition can be administered at least 15 minutes, prior to administration of the at least one pegylated therapeutic composition. In yet another aspect, the at least one high molecular weight PEG composition can be administered at least 20 minutes, prior to administration of the at least one pegylated therapeutic composition. In yet another aspect, the at least one high molecular weight PEG composition can be administered at least 25 minutes, prior to administration of the at least one pegylated therapeutic composition. In yet another aspect, the at least one high molecular weight PEG composition can be administered at least 30 minutes, prior to administration of the at least one pegylated therapeutic composition. In yet another aspect, the at least one high molecular weight PEG composition can be administered at least 40 minutes, prior to administration of the at least one pegylated therapeutic composition. In yet another aspect, the at least one high molecular weight PEG composition can be administered at least 45 minutes, prior to administration of the at least one pegylated therapeutic composition. In yet another aspect, the at least one high molecular weight PEG composition can be administered at least 50 minutes, prior to administration of the at least one pegylated therapeutic composition. In yet another aspect, the at least one high molecular weight PEG composition can be administered at least 60 minutes, prior to administration of the at least one pegylated therapeutic composition. In yet another aspect, the at least one high molecular weight PEG composition can be administered at least 90 minutes, prior to administration of the at least one pegylated therapeutic composition. In yet another aspect, the at least one high molecular weight PEG composition can be administered at least 2 hours, prior to administration of the at least one pegylated therapeutic composition. In yet another aspect, the at least one high molecular weight PEG composition can be administered at least 3 hours, prior to administration of the at least one pegylated therapeutic composition. In yet another aspect, the at least one high molecular weight PEG composition can be administered at least 4 hours, prior to administration of the at least one pegylated therapeutic composition. In yet another aspect, the at least one high molecular weight PEG composition can be administered at least 5 hours, prior to administration of the at least one pegylated therapeutic composition. In yet another aspect, the at least one high molecular weight PEG composition can be administered at least 6 hours, prior to administration of the at least one pegylated therapeutic composition. In yet another aspect, the at least one high molecular weight PEG composition can be administered at least 7 hours, prior to administration of the at least one pegylated therapeutic composition. In yet another aspect, the at least one high molecular weight PEG composition can be administered at least 8 hours, prior to administration of the at least one pegylated therapeutic composition. In yet another aspect, the at least one high molecular weight PEG composition can be administered at least 9 hours, prior to administration of the at least one pegylated therapeutic composition. In yet another aspect, the at least one high molecular weight PEG composition can be administered at least 10 hours, prior to administration of the at least one pegylated therapeutic composition. In yet another aspect, the at least one high molecular weight PEG composition can be administered at least 11 hours, prior to administration of the at least one pegylated therapeutic composition. In yet another aspect, the at least one high molecular weight PEG composition can be administered at least 12 hours, prior to administration of the at least one pegylated therapeutic composition. In yet another aspect, the at least one high molecular weight PEG composition can be administered at least 13 hours, prior to administration of the at least one pegylated therapeutic composition. In yet another aspect, the at least one high molecular weight PEG composition can be administered at least 14 hours, prior to administration of the at least one pegylated therapeutic composition. In yet another aspect, the at least one high molecular weight PEG composition can be administered at least 15 hours, prior to administration of the at least one pegylated therapeutic composition. In yet another aspect, the at least one high molecular weight PEG composition can be administered at least 16 hours, prior to administration of the at least one pegylated therapeutic composition. In yet another aspect, the at least one high molecular weight PEG composition can be administered at least 17 hours, prior to administration of the at least one pegylated therapeutic composition. In yet another aspect, the at least one high molecular weight PEG composition can be administered at least 18 hours, prior to administration of the at least one pegylated therapeutic composition. In yet another aspect, the at least one high molecular weight PEG composition can be administered at least 19 hours, prior to administration of the at least one pegylated therapeutic composition. In yet another aspect, the at least one high molecular weight PEG composition can be administered at least 20 hours, prior to administration of the at least one pegylated therapeutic composition. In yet another aspect, the at least one high molecular weight PEG composition can be administered at least 21 hours, prior to administration of the at least one pegylated therapeutic composition. In yet another aspect, the at least one high molecular weight PEG composition can be administered at least 22 hours, prior to administration of the at least one pegylated therapeutic composition. In yet another aspect, the at least one high molecular weight PEG composition can be administered at least 23 hours, prior to administration of the at least one pegylated therapeutic composition. In yet another aspect, the at least one high molecular weight PEG composition can be administered at least 24 hours, prior to administration of the at least one pegylated therapeutic composition.

The disease in need of treatment thereof is not critical. For example, the disease could be any type, kind, form and/or stage of cancer, rheumatoid arthritis, ulcerative colitis, Crohn's disease, asthma, COPD, diabetes, ischemia disease, renal disease, kidney disease, gout, etc. In one aspect, the disease is cancer. Examples of cancers include breast cancer, cervical cancer, ovary cancer, endometrial cancer, melanoma, uveal melanoma, brain tumor, lung cancer, liver cancer, lymphoma, neuroepithelioma, kidney cancer, bladder cancer, pancreatic cancer, prostate cancer, stomach cancer, colon cancer, uterus cancer, hematopoietic tumors of lymphoid lineage, myeloid leukemia, thyroid cancer, thyroid follicular cancer, myelodysplastic syndrome (MDS), tumor of mesenchymal origin, teratcarcinoma, neuroblastoma, glioma, glioblastoma, keratoacanthomas, analplastic large cell lymphoma, esophageal squamous cell carcinoma, follicular dentritic cell carcinoma, intestinal cancer, muscle invasive cancer, seminal vesicle tumor, epidermal carcinoma, spleen cancer, head and neck cancer, stomach cancer, bone cancer, cancer of retina, biliary cancer, small bowel cancer, salivary gland cancer, uterine sarcoma, cancer of testicles, cancer of connective tissue, prostatic hypertrophy, myelodysplasia, Waldenstrom's macroglobulinemia, nasopharyngeal, neuroendocrine cancer, mesothelioma, angiosarcoma, Kaposi's sarcoma, oesophagogastric, fallopian tube cancer, peritoneal cancer, papillary serous mullerian cancer, malignant ascites, gastrointestinal stromal tumor (GIST), Li-Fraumeni syndrome or Von Hippel-Lindau syndrome (VHL). The hematopoietic tumors of lymphoid lineage may be any of leukemia, acute lymphocytic leukemia, chronic lymphocytic leukemia, B-cell lymphoma, Burkitt's lymphoma, multiple myeloma, Hodgkin's lymphoma, or Non-Hodgkin's lymphoma. The myeloid leukemia may be acute myelogenous leukemia (AML) or chronic myelogenous leukemia (CML). A tumor of mesenchymal origin can include fibrosarcomas or rhabdomyosarcomas.

As mentioned previously herein, the method of the present disclosure improves and/or increases the circulation or circulating half-life of at least one pegylated therapeutic composition that is to be repeatedly administered to a subject suffering from a disease. For example, in the case where a subject has previously been administered at least one pegylated therapeutic composition which was determined to be quickly cleared (which is thought to be due to anti-PEG antibodies), a treating physician would know that administration of at least one high molecular weight PEG composition was working (and hence efficacious) if the subsequent dose of the at least one pegylated therapeutic composition was not quickly cleared, as determined by either a direct measurement of drug concentration in the subject, drug activity (such as via the use of an enzymatic assay), improvement in a disease marker (such as by the reduction in plasma concentrations of uric acid) or overall improvement in the disease being treated in the subject.

Additionally, the at least one high molecular weight PEG composition can be administered to the subject as frequently or infrequently as needed as determined by the treating physician based on the extent of the improvement or increase in the circulation or circulating half-life of the at least one pegylated therapeutic composition. The treating physician can monitor the subject during the course of treatment using routine techniques known in the art and make any clinical adjustments as necessary.

Methods of Restoring the Pharmacokinetic Profile of at Least One Pegylated Therapeutic Composition In yet another aspect, the present disclosure relates to methods of restoring or improving the pharmacokinetics or pharmacokinetic profile of at least one pegylated therapeutic composition that will, has been or will continue to be administered (or repeatedly administered) to a subject that is suffering from a disease and in need of treatment or continued treatment thereof. Specifically, the method involves administering to the subject in need of treatment or continued treatment, an effective amount of at least one high molecular weight PEG composition at an appropriate period or time point(s) prior to and/or during the course of treatment. While not wishing to be bound by any theory, it is believed that the administration of one or more high molecular weight PEG compositions saturates at least some or a certain percentage of the circulating anti-PEG antibodies in the subject thereby preventing, inhibiting and/or interfering with their (competitive) binding and/or interaction with the one or more pegylated therapeutic compositions.

In one aspect, the subject being treated pursuant to the method described herein has not yet been administered at least one pegylated therapeutic composition for treatment of the disease. Under such a circumstance, the subject may be administered at least one high molecular weight PEG composition prophylactically, in advance of treatment, to assist in restoring and/or improving the pharmacokinetic or pharmacokinetic profile of the at least one pegylated therapeutic composition once the composition is ultimately administered to the subject. For example, the treating physician may know or may have determined (using routine techniques known in the art) that the subject has a high-titer of circulating anti-PEG antibodies or pre-existing circulating anti-PEG antibodies (prior to beginning the treatment). Alternatively, the circulating anti-PEG antibody titer level of the subject may not be known or may not have been determined.

In another aspect, the subject being treated pursuant to the method described herein may have been receiving treatment with a specific pegylated therapeutic composition (a "first" pegylated therapeutic composition) and is being switched to a second pegylated therapeutic composition (a "second" pegylated therapeutic composition). In such circumstances, the subject can be administered an effective amount of the at least one high molecular weight PEG composition between administration of the first and second pegylated therapeutic compositions.

Still a further aspect, the subject being treated pursuant to the method described herein may have previously received one or more administrations of the at least one pegylated therapeutic composition. Said another way, the subject is receiving repeated administrations of the at least one pegylated therapeutic composition. Under such a circumstance, the at least one high molecular weight PEG composition is administered to the subject prior to any subsequent or further administration of any (additional) pegylated therapeutic compositions in order to assist in restoring and/or improving the pharmacokinetic or pharmacokinetic profile, particularly in instances where the circulating half-life of the pegylated therapeutic composition has been determined (using routine techniques known in the art) to have been reduced thus impacting the efficacy of the pegylated therapeutic composition to treat the disease. The at least one high molecular PEG composition can be administered at any period or time point(s) prior to any subsequent or further administration of the at least one pegylated therapeutic composition. Alternatively, the high molecular weight PEG composition can be administered to the subject simultaneously with the administration of the at least one pegylated therapeutic composition. For example, the at least one high molecular weight PEG composition can be co-administered with the at least one pegylated therapeutic composition. For example, the at least one high molecular weight PEG may be included as part of the composition comprising the pegylated therapeutic such that both the high molecular weight PEG and pegylated therapeutic are administered together as a single formulation or composition. Such a formulation or composition can be prepared using routine techniques known in the art.

As mentioned previously, the method of the present disclosure involves administering an effective amount of at least one high molecular weight PEG composition to a subject suffering from a disease and in need of treatment or continued treatment thereof. Methods for determining an effective amount of at least one high molecular weight PEG composition to administer to the subject can be determined by the treating physician using routine techniques known in the art. For example, an effective amount of the at least one high molecular weight PEG can be from about 1 to about 2500 milligrams per kilogram of the subject. Alternatively, 10 to about 2500 milligrams per kilogram of the subject. Alternatively, 25 to about 2500 milligrams per kilogram of the subject. Still further alternatively, the effective amount can be from about 50 to about 2500 milligrams per kilogram of the subject. Still further alternatively, the effective amount can be from about 100 to about 2500 milligrams per kilogram of the subject. Still further alternatively, the effective amount can be from about 1 to about 2200 milligrams per kilogram of the subject. Still further alternatively, the effective amount can be from about 10 to about 2200 milligrams per kilogram of the subject. Still further alternatively, the effective amount can be from about 25 to about 2200 milligrams per kilogram of the subject. Still further alternatively, the effective amount can be from about 50 to about 2200 milligrams per kilogram of the subject. Still further alternatively, the effective amount can be from about 100 to about 2200 milligrams per kilogram of the subject. Still further alternatively, the effective amount can be from about 1 to about 2000 milligrams per kilogram of the subject. Still further alternatively, the effective amount can be from about 10 to about 2000 milligrams per kilogram of the subject. Still further alternatively, the effective amount can be from about 25 to about 2000 milligrams per kilogram of the subject. Still further alternatively, the effective amount can be from about 50 to about 2000 milligrams per kilogram of the subject. Still further alternatively, the effective amount can be from about 100 to about 2000 milligrams per kilogram of the subject. Still further alternatively, the effective amount can be from about 1 to about 1500 milligrams per kilogram of the subject. Still further alternatively, the effective amount can be from about 10 to about 1500 milligrams per kilogram of the subject. Still further alternatively, the effective amount can be from about 25 to about 1500 milligrams per kilogram of the subject. Still further alternatively, the effective amount can be from about 50 to about 1500 milligrams per kilogram of the subject. Still further alternatively, the effective amount can be from about 100 to about 1500 milligrams per kilogram of the subject. Still further alternatively, the effective amount can be from about 1 to about 1000 milligrams per kilogram of the subject. Still further alternatively, the effective amount can be from about 10 to about 1000 milligrams per kilogram of the subject. Still further alternatively, the effective amount can be from about 25 to about 1000 milligrams per kilogram of the subject. Still further alternatively, the effective amount can be from about 50 to about 1000 milligrams per kilogram of the subject. Still further alternatively, the effective amount can be from about 100 to about 1000 milligrams per kilogram of the subject. Still further alternatively, the effective amount can be from about 1 to about 750 milligrams per kilogram of the subject. Still further alternatively, the effective amount can be from about 10 to about 750 milligrams per kilogram of the subject. Still further alternatively, the effective amount can be from about 25 to about 750 milligrams per kilogram of the subject. Still further alternatively, the effective amount can be from about 50 to about 750 milligrams per kilogram of the subject. Still further alternatively, the effective amount can be from about 100 to about 750 milligrams per kilogram of the subject. Still further alternatively, the effective amount can be from about 1 to about 500 milligrams per kilogram of the subject. Still further alternatively, the effective amount can be from about 10 to about 500 milligrams per kilogram of the subject. Still further alternatively, the effective amount can be from about 25 to about 500 milligrams per kilogram of the subject. Still further alternatively, the effective amount can be from about 50 to about 500 milligrams per kilogram of the subject. Still further alternatively, the effective amount can be from about 100 to about 500 milligrams per kilogram of the subject.

In aspects when the high molecular weight PEG is to be administered to the subject prior to the administration of at least one pegylated therapeutic composition (regardless of whether the at least one pegylated therapeutic composition has not yet been administered previously to the subject and/or if the administration of the at least one pegylated therapeutic composition is subsequent or further to a previous administration(s) of the at least one pegylated therapeutic composition), then at least one high molecular weight PEG composition can be administered at least 5 seconds, at least seconds, at least 15 seconds, at least 20 seconds, at least 30 seconds, at least 60 seconds, at least seconds, at least 2 minutes, at least 3 minutes, at least 4 minutes, at least 5 minutes, at least 10 minutes, at least 15 minutes, at least 20 minutes, at least 25 minutes, at least 30 minutes, at least 40 minutes, at least 45 minutes, at least 50 minutes, at least 60 minutes, at least 90 minutes, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours prior to administration of the at least one pegylated therapeutic composition. In one aspect, the at least one high molecular weight PEG composition can be administered at least 5 seconds prior to administration of the at least one pegylated therapeutic composition. In another aspect, the at least one high molecular weight PEG composition can be administered at least 5 seconds prior to administration of the at least one pegylated therapeutic composition. In yet another aspect, the at least one high molecular weight PEG composition can be administered at least 10 seconds prior to administration of the at least one pegylated therapeutic composition. In yet another aspect, the at least one high molecular weight PEG composition can be administered at least 15 seconds prior to administration of the at least one pegylated therapeutic composition. In yet another aspect, the at least one high molecular weight PEG composition can be administered at least 20 seconds prior to administration of the at least one pegylated therapeutic composition. In yet another aspect, the at least one high molecular weight PEG composition can be administered at least 30 seconds prior to administration of the at least one pegylated therapeutic composition. In yet another aspect, the at least one high molecular weight PEG composition can be administered at least 60 seconds prior to administration of the at least one pegylated therapeutic composition. In yet another aspect, the at least one high molecular weight PEG composition can be administered at least 90 seconds prior to administration of the at least one pegylated therapeutic composition. In yet another aspect, the at least one high molecular weight PEG composition can be administered at least 2 minutes, prior to administration of the at least one pegylated therapeutic composition. In yet another aspect, the at least one high molecular weight PEG composition can be administered at least 3 minutes, prior to administration of the at least one pegylated therapeutic composition. In yet another aspect, the at least one high molecular weight PEG composition can be administered at least 3 minutes, prior to administration of the at least one pegylated therapeutic composition. In yet another aspect, the at least one high molecular weight PEG composition can be administered at least 4 minutes, prior to administration of the at least one pegylated therapeutic composition. In yet another aspect, the at least one high molecular weight PEG composition can be administered at least 5 minutes, prior to administration of the at least one pegylated therapeutic composition. In yet another aspect, the at least one high molecular weight PEG composition can be administered at least 10 minutes, prior to administration of the at least one pegylated therapeutic composition. In yet another aspect, the at least one high molecular weight PEG composition can be administered at least 15 minutes, prior to administration of the at least one pegylated therapeutic composition. In yet another aspect, the at least one high molecular weight PEG composition can be administered at least 20 minutes, prior to administration of the at least one pegylated therapeutic composition. In yet another aspect, the at least one high molecular weight PEG composition can be administered at least 25 minutes, prior to administration of the at least one pegylated therapeutic composition. In yet another aspect, the at least one high molecular weight PEG composition can be administered at least 30 minutes, prior to administration of the at least one pegylated therapeutic composition. In yet another aspect, the at least one high molecular weight PEG composition can be administered at least 40 minutes, prior to administration of the at least one pegylated therapeutic composition. In yet another aspect, the at least one high molecular weight PEG composition can be administered at least 45 minutes, prior to administration of the at least one pegylated therapeutic composition. In yet another aspect, the at least one high molecular weight PEG composition can be administered at least 50 minutes, prior to administration of the at least one pegylated therapeutic composition. In yet another aspect, the at least one high molecular weight PEG composition can be administered at least 60 minutes, prior to administration of the at least one pegylated therapeutic composition. In yet another aspect, the at least one high molecular weight PEG composition can be administered at least 90 minutes, prior to administration of the at least one pegylated therapeutic composition. In yet another aspect, the at least one high molecular weight PEG composition can be administered at least 2 hours, prior to administration of the at least one pegylated therapeutic composition. In yet another aspect, the at least one high molecular weight PEG composition can be administered at least 3 hours, prior to administration of the at least one pegylated therapeutic composition. In yet another aspect, the at least one high molecular weight PEG composition can be administered at least 4 hours, prior to administration of the at least one pegylated therapeutic composition. In yet another aspect, the at least one high molecular weight PEG composition can be administered at least 5 hours, prior to administration of the at least one pegylated therapeutic composition. In yet another aspect, the at least one high molecular weight PEG composition can be administered at least 6 hours, prior to administration of the at least one pegylated therapeutic composition. In yet another aspect, the at least one high molecular weight PEG composition can be administered at least 7 hours, prior to administration of the at least one pegylated therapeutic composition. In yet another aspect, the at least one high molecular weight PEG composition can be administered at least 8 hours, prior to administration of the at least one pegylated therapeutic composition. In yet another aspect, the at least one high molecular weight PEG composition can be administered at least 9 hours, prior to administration of the at least one pegylated therapeutic composition. In yet another aspect, the at least one high molecular weight PEG composition can be administered at least 10 hours, prior to administration of the at least one pegylated therapeutic composition. In yet another aspect, the at least one high molecular weight PEG composition can be administered at least 11 hours, prior to administration of the at least one pegylated therapeutic composition. In yet another aspect, the at least one high molecular weight PEG composition can be administered at least 12 hours, prior to administration of the at least one pegylated therapeutic composition. In yet another aspect, the at least one high molecular weight PEG composition can be administered at least 13 hours, prior to administration of the at least one pegylated therapeutic composition. In yet another aspect, the at least one high molecular weight PEG composition can be administered at least 14 hours, prior to administration of the at least one pegylated therapeutic composition. In yet another aspect, the at least one high molecular weight PEG composition can be administered at least 15 hours, prior to administration of the at least one pegylated therapeutic composition. In yet another aspect, the at least one high molecular weight PEG composition can be administered at least 16 hours, prior to administration of the at least one pegylated therapeutic composition. In yet another aspect, the at least one high molecular weight PEG composition can be administered at least 17 hours, prior to administration of the at least one pegylated therapeutic composition. In yet another aspect, the at least one high molecular weight PEG composition can be administered at least 18 hours, prior to administration of the at least one pegylated therapeutic composition. In yet another aspect, the at least one high molecular weight PEG composition can be administered at least 19 hours, prior to administration of the at least one pegylated therapeutic composition. In yet another aspect, the at least one high molecular weight PEG composition can be administered at least 20 hours, prior to administration of the at least one pegylated therapeutic composition. In yet another aspect, the at least one high molecular weight PEG composition can be administered at least 21 hours, prior to administration of the at least one pegylated therapeutic composition. In yet another aspect, the at least one high molecular weight PEG composition can be administered at least 22 hours, prior to administration of the at least one pegylated therapeutic composition. In yet another aspect, the at least one high molecular weight PEG composition can be administered at least 23 hours, prior to administration of the at least one pegylated therapeutic composition. In yet another aspect, the at least one high molecular weight PEG composition can be administered at least 24 hours, prior to administration of the at least one pegylated therapeutic composition.

The disease in need of treatment thereof is not critical. For example, the disease could be any type, kind, form and/or stage of cancer, rheumatoid arthritis, ulcerative colitis, Crohn's disease, asthma, COPD, diabetes, ischemia disease, renal disease, kidney disease, gout, etc. In one aspect, the disease is cancer. Examples of cancers include breast cancer, cervical cancer, ovary cancer, endometrial cancer, melanoma, uveal melanoma, brain tumor, lung cancer, liver cancer, lymphoma, neuroepithelioma, kidney cancer, bladder cancer, pancreatic cancer, prostate cancer, stomach cancer, colon cancer, uterus cancer, hematopoietic tumors of lymphoid lineage, myeloid leukemia, thyroid cancer, thyroid follicular cancer, myelodysplastic syndrome (MDS), tumor of mesenchymal origin, teratcarcinoma, neuroblastoma, glioma, glioblastoma, keratoacanthomas, analplastic large cell lymphoma, esophageal squamous cell carcinoma, follicular dentritic cell carcinoma, intestinal cancer, muscle invasive cancer, seminal vesicle tumor, epidermal carcinoma, spleen cancer, head and neck cancer, stomach cancer, bone cancer, cancer of retina, biliary cancer, small bowel cancer, salivary gland cancer, uterine sarcoma, cancer of testicles, cancer of connective tissue, prostatic hypertrophy, myelodysplasia, Waldenstrom's macroglobulinemia, nasopharyngeal, neuroendocrine cancer, mesothelioma, angiosarcoma, Kaposi's sarcoma, oesophagogastric, fallopian tube cancer, peritoneal cancer, papillary serous mullerian cancer, malignant ascites, gastrointestinal stromal tumor (GIST), Li-Fraumeni syndrome or Von Hippel-Lindau syndrome (VHL). The hematopoietic tumors of lymphoid lineage may be any of leukemia, acute lymphocytic leukemia, chronic lymphocytic leukemia, B-cell lymphoma, Burkitt's lymphoma, multiple myeloma, Hodgkin's lymphoma, or Non-Hodgkin's lymphoma. The myeloid leukemia may be acute myelogenous leukemia (AML) or chronic myelogenous leukemia (CML). A tumor of mesenchymal origin can include fibrosarcomas or rhabdomyosarcomas.

As mentioned previously herein, the method of the present disclosure restores and/or improves the pharmacokinetics or pharmacokinetic profile of at least one pegylated therapeutic composition that is to be repeatedly administered to a subject suffering from a disease. Methods for determining the pharmacokinetics or pharmacokinetic profile of at least one pegylated therapeutic composition can be done using routine techniques known in the art. For example, one skilled in the art could examine one or more of the maximum concentrations that the pegylated therapeutic composition attains (C max), the time at which this maximum occurs (T max), and the area under the concentration-versus-time curve (AUC) to determine whether or not the pharmacokinetics or pharmacokinetic profile of the at least one pegylated therapeutic composition has been restored or improved. Methods for determining C max, T max and AUC are routine and well known to those skilled in the art.

Additionally, the at least one high molecular weight PEG composition can be administered to the subject as frequently or infrequently as needed as determined by the treating physician based on the extent of the improvement or increase in the circulation or circulating half-life of the at least one pegylated therapeutic composition. The treating physician can monitor the subject during the course of treatment using routine techniques known in the art and make any clinical adjustments as necessary.

Methods of Reducing or Attenuating the Formation of anti-PEG Antibodies in a Subject Requiring or Continuing to Require Treatment In still yet another aspect, the present disclosure relates to methods of reducing or attenuating the formation of anti-PEG antibodies or a high-titer of anti-PEG antibodies in a subject suffering from a disease and in need of treatment or continued treatment thereof. Specifically, the method involves administering to the subject in need of treatment or continued treatment, an effective amount of (a) at least one high molecular weight PEG composition; (b) at least one low molecular weight PEG composition; or (c) any combination of (a) and (b) at an appropriate period or time point(s) prior to and/or during the course of treatment to prevent the formation or development of anti-PEG antibodies or a high-titer of anti-PEG antibodies in the subject.

In one aspect, the subject being treated pursuant to the method described herein has not yet been administered at least one pegylated therapeutic composition for treatment of the disease. Under such a circumstance, the subject may be administered at least one high molecular weight PEG composition, at least one low molecular weight PEG composition or a combination of at least one high molecular weight PEG composition and at least one low molecular weight PEG composition prophylactically, in advance of treatment, prior to administration of the at least one pegylated therapeutic composition to the subject.

In another aspect, the subject being treated pursuant to the method described herein may have been receiving treatment with a specific pegylated therapeutic composition (a "first" pegylated therapeutic composition) and is being switched to a second pegylated therapeutic composition (a "second" pegylated therapeutic composition). In such circumstances, the subject can be administered an effective amount of the at least one high molecular weight PEG composition, at least one low molecular weight PEG composition or a combination of at least one high molecular weight PEG composition and at least one low molecular weight PEG composition between administration of the first and second pegylated therapeutic compositions.

Still a further aspect, the subject being treated pursuant to the method described herein may have previously received one or more administrations of the at least one pegylated therapeutic composition. Said another way, the subject is receiving repeated administrations of the at least one pegylated therapeutic composition. Under such a circumstance, the at least one high molecular weight PEG composition, at least one low molecular weight PEG composition or a combination of at least one high molecular weight PEG composition and at least one low molecular weight PEG composition is administered to the subject prior to any subsequent or further administration of any (additional) pegylated therapeutic compositions in order to prevent the formation of any anti-PEG antibodies. The at least one high molecular weight PEG composition, at least one low molecular weight PEG composition or a combination of at least one high molecular weight PEG composition and at least one low molecular weight PEG composition can be administered at any period or time point(s) prior to any subsequent or further administration of the at least one pegylated therapeutic composition. Alternatively, the at least one high molecular weight PEG composition, at least one low molecular weight PEG composition or a combination of at least one high molecular weight PEG composition and at least one low molecular weight PEG composition can be administered to the subject simultaneously with the administration of the at least one pegylated therapeutic composition. For example, the at least one high molecular weight PEG composition, at least one low molecular weight PEG composition or a combination of at least one high molecular weight PEG composition and at least one low molecular weight PEG composition can be co-administered with the at least one pegylated therapeutic composition. For example, the at least one high molecular weight PEG, at least one low molecular weight PEG or combination of at least one high molecular weight PEG and at least one low molecular weight PEG may be included as part of the composition comprising the pegylated therapeutic such that both the high molecular weight PEG, low molecular weight PEG or combination of high molecular weight PEG and low molecular weight PEG and pegylated therapeutic are administered together as a single formulation or composition. Such a formulation or composition can be prepared using routine techniques known in the art.

As mentioned previously, the method of the present disclosure involves administering an effective amount of at least one high molecular weight PEG composition, at least one low molecular weight PEG composition or a combination of at least one high molecular weight PEG composition and at least one low molecular weight PEG composition to a subject suffering from a disease and in need of treatment or continued treatment thereof. Methods for determining an effective amount of at least one high molecular weight PEG composition, at least one low molecular weight PEG composition or a combination of at least one high molecular weight PEG composition and at least one low molecular weight PEG composition to administer to the subject can be determined by the treating physician using routine techniques known in the art. For example, an effective amount of the at least one high molecular weight PEG composition, at least one low molecular weight PEG composition or a combination of at least one high molecular weight PEG composition and at least one low molecular weight PEG composition can be from about 1 to about 2500 milligrams per kilogram of the subject. Alternatively, 25 to about 2500 milligrams per kilogram of the subject. Still further alternatively, the effective amount can be from about 50 to about 2500 milligrams per kilogram of the subject. Still further alternatively, the effective amount can be from about 100 to about 2500 milligrams per kilogram of the subject. Still further alternatively, the effective amount can be from about 1 to about 2200 milligrams per kilogram of the subject. Still further alternatively, the effective amount can be from about 10 to about 2200 milligrams per kilogram of the subject. Still further alternatively, the effective amount can be from about 25 to about 2200 milligrams per kilogram of the subject. Still further alternatively, the effective amount can be from about 50 to about 2200 milligrams per kilogram of the subject. Still further alternatively, the effective amount can be from about 100 to about 2200 milligrams per kilogram of the subject. Still further alternatively, the effective amount can be from about 10 to about 2000 milligrams per kilogram of the subject. Still further alternatively, the effective amount can be from about 10 to about 2000 milligrams per kilogram of the subject. Still further alternatively, the effective amount can be from about 25 to about 2000 milligrams per kilogram of the subject. Still further alternatively, the effective amount can be from about 50 to about 2000 milligrams per kilogram of the subject. Still further alternatively, the effective amount can be from about 100 to about 2000 milligrams per kilogram of the subject. Still further alternatively, the effective amount can be from about 1 to about 1500 milligrams per kilogram of the subject. Still further alternatively, the effective amount can be from about 10 to about 1500 milligrams per kilogram of the subject. Still further alternatively, the effective amount can be from about 25 to about 1500 milligrams per kilogram of the subject. Still further alternatively, the effective amount can be from about 50 to about 1500 milligrams per kilogram of the subject. Still further alternatively, the effective amount can be from about 100 to about 1500 milligrams per kilogram of the subject. Still further alternatively, the effective amount can be from about 1 to about 1000 milligrams per kilogram of the subject. Still further alternatively, the effective amount can be from about 10 to about 1000 milligrams per kilogram of the subject. Still further alternatively, the effective amount can be from about 25 to about 1000 milligrams per kilogram of the subject. Still further alternatively, the effective amount can be from about 50 to about 1000 milligrams per kilogram of the subject. Still further alternatively, the effective amount can be from about 100 to about 1000 milligrams per kilogram of the subject. Still further alternatively, the effective amount can be from about 1 to about 750 milligrams per kilogram of the subject. Still further alternatively, the effective amount can be from about 10 to about 750 milligrams per kilogram of the subject. Still further alternatively, the effective amount can be from about 25 to about 750 milligrams per kilogram of the subject. Still further alternatively, the effective amount can be from about 50 to about 750 milligrams per kilogram of the subject. Still further alternatively, the effective amount can be from about 100 to about 750 milligrams per kilogram of the subject. Still further alternatively, the effective amount can be from about 1 to about 500 milligrams per kilogram of the subject. Still further alternatively, the effective amount can be from about 10 to about 500 milligrams per kilogram of the subject. Still further alternatively, the effective amount can be from about 25 to about 500 milligrams per kilogram of the subject. Still further alternatively, the effective amount can be from about 50 to about 500 milligrams per kilogram of the subject. Still further alternatively, the effective amount can be from about 100 to about 500 milligrams per kilogram of the subject.

In aspects when the high molecular weight PEG composition, low molecular weight PEG or a combination of the high molecular weight PEG composition and the low molecular weight composition is to be administered to the subject prior to the administration of at least one pegylated therapeutic composition (regardless of whether the at least one pegylated therapeutic composition has not yet been administered previously to the subject and/or if the administration of the at least one pegylated therapeutic composition is subsequent or further to a previous administration(s) of the at least one pegylated therapeutic composition), then the at least one high molecular weight PEG composition, at least one low molecular weight PEG composition or a combination of at least one high molecular weight PEG composition and at least one low molecular weight PEG composition can be administered at least 5 seconds, at least 10 seconds, at least 15 seconds, at least 20 seconds, at least 30 seconds, at least 60 seconds, at least 90 seconds, at least 2 minutes, at least 3 minutes, at least 4 minutes, at least 5 minutes, at least 10 minutes, at least 15 minutes, at least 20 minutes, at least 25 minutes, at least 30 minutes, at least 40 minutes, at least 45 minutes, at least 50 minutes, at least 60 minutes, at least 90 minutes, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours prior to administration of the at least one pegylated therapeutic composition. In one aspect, the at least one high molecular weight PEG composition, at least one low molecular weight PEG composition or a combination of at least one high molecular weight PEG composition and at least one low molecular weight PEG composition can be administered at least 5 seconds prior to administration of the at least one pegylated therapeutic composition. In another aspect, the at least one high molecular weight PEG composition, at least one low molecular weight PEG composition or a combination of at least one high molecular weight PEG composition and at least one low molecular weight PEG composition can be administered at least 5 seconds prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 10 seconds prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 15 seconds prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 20 seconds prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 30 seconds prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 60 seconds prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 90 seconds prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 2 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 3 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 3 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 4 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 5 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 10 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 15 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 20 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 25 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 30 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 40 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 45 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 50 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 60 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 90 minutes, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 2 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 3 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 4 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 5 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 6 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 7 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 8 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 9 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 10 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 11 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 12 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 13 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 14 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 15 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 16 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 17 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 18 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 19 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 20 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 21 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 22 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 23 hours, prior to administration of the at least one pegylated therapeutic composition. In yet another aspect, the at least one high molecular weight PEG composition, at least one low molecular weight PEG composition or a combination of at least one high molecular weight PEG composition and at least one low molecular weight PEG composition can be administered at least 24 hours, prior to administration of the at least one pegylated therapeutic composition.

The disease in need of treatment thereof is not critical. For example, the disease could be any type, kind, form and/or stage of cancer, rheumatoid arthritis, ulcerative colitis, Crohn's disease, asthma, COPD, diabetes, ischemia disease, renal disease, kidney disease, gout, etc. In one aspect, the disease is cancer. Examples of cancers include breast cancer, cervical cancer, ovary cancer, endometrial cancer, melanoma, uveal melanoma, brain tumor, lung cancer, liver cancer, lymphoma, neuroepithelioma, kidney cancer, bladder cancer, pancreatic cancer, prostate cancer, stomach cancer, colon cancer, uterus cancer, hematopoietic tumors of lymphoid lineage, myeloid leukemia, thyroid cancer, thyroid follicular cancer, myelodysplastic syndrome (MDS), tumor of mesenchymal origin, teratcarcinoma, neuroblastoma, glioma, glioblastoma, keratoacanthomas, analplastic large cell lymphoma, esophageal squamous cell carcinoma, follicular dentritic cell carcinoma, intestinal cancer, muscle invasive cancer, seminal vesicle tumor, epidermal carcinoma, spleen cancer, head and neck cancer, stomach cancer, bone cancer, cancer of retina, biliary cancer, small bowel cancer, salivary gland cancer, uterine sarcoma, cancer of testicles, cancer of connective tissue, prostatic hypertrophy, myelodysplasia, Waldenstrom's macroglobulinemia, nasopharyngeal, neuroendocrine cancer, mesothelioma, angiosarcoma, Kaposi's sarcoma, oesophagogastric, fallopian tube cancer, peritoneal cancer, papillary serous mullerian cancer, malignant ascites, gastrointestinal stromal tumor (GIST), Li-Fraumeni syndrome or Von Hippel-Lindau syndrome (VHL). The hematopoietic tumors of lymphoid lineage may be any of leukemia, acute lymphocytic leukemia, chronic lymphocytic leukemia, B-cell lymphoma, Burkitt's lymphoma, multiple myeloma, Hodgkin's lymphoma, or Non-Hodgkin's lymphoma. The myeloid leukemia may be acute myelogenous leukemia (AML) or chronic myelogenous leukemia (CML). A tumor of mesenchymal origin can include fibrosarcomas or rhabdomyosarcomas.

Additionally, the at least one high molecular weight PEG composition, at least one low molecular weight PEG composition or a combination of at least one high molecular weight PEG composition and at least one low molecular weight PEG composition can be administered to the subject as frequently or infrequently as needed as determined by the treating physician. The treating physician can monitor the subject during the course of treatment using routine techniques known in the art and make any clinical adjustments as necessary.

The present disclosure has multiple aspects, illustrated by the following non-limiting examples.

EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties. The present disclosure has multiple aspects, illustrated by the following non-limiting examples.

Example 1: Use of Free PEG as a Therapeutic Intervention to Overcome Existing anti-PEG Antibodies Mouse Model of PEGylated Liposomal Doxorubicin (PLD) Clearance Adult BALB/c mice (18-22 weeks, female, Charles River) were passively immunized with APA by the intravenous administration of mouse anti-PEG IgG1 (Silver Lake Research, CH2076, lot K0868) 24 hours prior to the intravenous administration of PLD (3 mg/kg, Doxil®, Janssen Products, LP). Two doses of APA were tested in mice, administered intravenously: 1) 3 ug, which resulted in a plasma concentration of ~300 ng/mL 24 hours later, at the time of PLD injection, and 2) 30 ug, which resulted in a plasma concentration of about 7 ug/mL at the time of PLD injection. In some groups, free PEG was administered intravenously (550 mg/kg) to mice 0.5 hours prior to the administration of PLD (3 mg/kg). Other groups received PBS 0.5 hours prior to the administration of PLD as a control. At time points of 0.083, 3, 6, 24, 48, and 96 hours following PLD administration, mice were anesthetized using ketamine (100 mg/kg, i.p.) and medetomidine hydrochloride (1 mg/kg, i.p.), then sacrificed via cardiac puncture (into sodium heparin vacutainers) and cervical dislocation. The blood, liver, spleen, and lungs were collected for doxorubicin quantification.

PLD Quantification

The complete methods for sample collection, preparation and analysis of encapsulated and released doxorubicin in plasma and total (encapsulated+released) doxorubicin in tissues after administration of PLD have been previously described (See, Gabizon, A., R. Shiota, and D. Papahadjopoulos, Pharmacokinetics and tissue distribution of doxorubicin encapsulated in stable liposomes with long circulation times. J Natl Cancer Inst, 1989. 81(19): p. 1484-8; Amselem, S., A. Gabizon, and Y. Barenholz, Optimization and upscaling of doxorubicin-containing liposomes for clinical use. J Pharm Sci, 1990. 79(12): p. 1045-52; Zamboni, W. C., et al., Plasma, Tumor, and Tissue Disposition of STEALTH Liposomal CKD-602 (S-CKD602) and Nonliposomal CKD-602 in Mice Bearing A375 Human Melanoma Xenografts. Clinical Cancer Research, 2007. 13(23): p. 7217, and Anders, C. K., et al., Pharmacokinetics and efficacy of PEGylated liposomal doxorubicin in an intracranial model of breast cancer. PLoS One, 2013. 8(5): p. e61359.)

Briefly, blood samples were collected in sodium heparin tubes at 0.083, 3, 6, 24, 48 and 96 hours after the administration of PLD. Blood was centrifuged at 1,500 g for 5 minutes to obtain plasma. Encapsulated and released doxorubicin in plasma were separated using solid phase separation. Tissues of interest were flash frozen in liquid nitrogen and stored at −80° C. until processing. Upon processing, tissues were thawed, weighed, and diluted in a 1:3 ratio with phosphate buffered saline prior to homogenizing with a Precellys 24 bead mill homogenizer (Omni International Inc, Kennesaw, GA). Samples were further processed by addition of 800 µL extraction solution (acetonitrile with 100 ng/mL daunorubicin internal standard) to 200 µL of plasma or tissue homogenate. The samples were vortexed for 10 minutes and centrifuged at 10,000 g for 10 minutes at 4° C. The supernatant was removed to a clean tube, evaporated to dryness under nitrogen, and reconstituted in 150 μl of 15% acetonitrile in water plus 0.1% formic acid. The samples were then vortexed, transferred to autosampler vials, and analyzed by high-performance liquid chromatography with fluorescence detection (HPLC-FL) set to excitation wavelength 490 nm/emission wavelength 590 nm. The HPLC-FL technique had a quantitative range of 10-3,000 ng/mL for sum total doxorubicin in tissues and released doxorubicin in plasma and 300-30,000 ng/mL for encapsulated doxorubicin in plasma. Samples that returned a concentration above the quantitative limit were diluted to fall within the quantitative range and reinjected.

Blood Pressure Measurement and Cardiac Rhythm Analysis

The blood pressure in BALB/c mice (8 months and 10 weeks, female) that were administered free PEG 40 kDa or PBS was measured. Some mice were vaccinated against PEG 4 weeks prior to free PEG injection and blood pressure measurement. APA responses were confirmed in these mice via competition ELISA. Blood pressure was measured using a pressure-volume measurement system (AVD 500, Scisense). Mice were anesthetized with 100 mg/kg ketamine and 15 mg/kg xylazine, administered intraperitoneally. Nair was used to remove fur from the anterior neck. The right carotid artery was dissected and ligated to prevent blood flow. A nick was made in the carotid artery inferior to the ligation, and a pressure transducer was inserted to the level of the innominate artery, near the aortic arch. Blood pressure was measured continuously. Baseline pressure measurements were recorded for one minute prior to the injection of polyethylene glycol 40 kDa at a dose of 550 mg/kg in PBS in approximately 150 μL total volume, and pressure was continuously recorded for minutes. Pulse rate was determined by the frequency of the arterial pressure change. Terminal blood was collected from the inferior vena cava. Treatment allocation of free PEG versus PBS was concealed to the research technicians administering injections as well as the pathologists conducting blood and tissue processing and analysis.

Immunohistochemistry and Clinical Blood Chemistry

BALB/c mice (8 weeks, female, Charles River) were administered free PEG40 kDa (550 mg/kg) or PBS (equal volume) weekly for six weeks. Experiments were conducted in both vaccinated and non-vaccinated animals. Three days following the final injection of free PEG, the mice were sacrificed and liver, kidney, and blood were collected. Organs were split in half, and each flash was either flash frozen for IHC or submerged in neutral buffered formalin for standard histology. Tissues were sectioned and stained per normal protocols. Clinical blood chemistry analyses, urine testing, and metabolic panels were conducted using [instrument]. Blood and urine samples were analyzed within 2 hours of collection, and were kept at 4° C. until analysis was conducted. Histological and clinical chemistry analyses were conducted by a blinded licensed pathologist. Toxicity studies were pre-registered at preclinicaltrials.eu.

Anti-PEG Antibody Quantification

APA concentrations in blood were measured as previously described (See, McSweeney, M. D., et al., A minimal physiologically based pharmacokinetic model that predicts anti-PEG IgG-mediated clearance of PEGylated drugs in human and mouse. Journal of Controlled Release, 2018. 284: p. 171-178). Briefly, whole blood, collected from facial bleed, was clotted at room temperature for 15 minutes and centrifuged at 2,000 g for 15 minutes to generate serum. Untreated half-area 96-well Costar plates (Corning #3695) were coated with 1,2-distearoyl-sn-glycero-3-phosphoethanolamine-methoxy PEG5 kDa (DSPE-PEG; Nanocs, New York, NY, USA) at 50 μg/mL in PBS overnight at 4C. The plates were blocked with 5% w/v milk in DPBS for 1 hour at room temperature. Plasma samples were diluted 20 to 50-fold in 1% milk in DPBS and added to the plate, 504 per well. The samples were plated in both the presence and absence of free PEG 10 kDa (final concentration 10 mg/mL) as competition, incubated at 4C overnight, and subsequently washed with DPBS. A standard curve was generated using anti-PEG IgG1 (Silver Lake Research, CH2076, lot K0868). Secondary antibodies were goat anti-mouse IgG-HRP (1:5,000 dilution, Santa Cruz, sc-2005, lot #D1816), with 1 step Ultra TMB (ThermoFisher) as substrate. The HRP reaction was quenched with 2N sulfuric acid, and the absorbance was read at 450 nm (signal) and 570 nm (background) using a Spectramax M2 plate reader (Molecular Devices). All washes were with DPBS without TWEEN. Sample absorbances were corrected for competition results to adjust for the effect of non-specific binding by non-APA antibodies and analyzed using a 5-parameter logistic regression.

Results

High MW free PEG rescues the pharmacokinetics of PEG-drugs in mice with APA

It has previously been established that PEGylated liposomal doxorubicin (PLD) can be used to investigate the accelerated blood clearance of PEGylated drugs mediated by passively infused APA, due to the ease of quantifying the fluorescent doxorubicin in plasma and tissues as well as the ability to accurately control APA levels (See, McSweeney, M. D., et al., A minimal physiologically based pharmacokinetic model that predicts anti-PEG IgG-mediated clearance of PEGylated drugs in human and mouse. Journal of Controlled Release, 2018. 284: p. 171-178; Hsieh, Y. C., et al., Pre-existing anti-polyethylene glycol antibody reduces the therapeutic efficacy and pharmacokinetics of PEGylated liposomes. Theranostics, 2018. 8(11): p. 3164-3175.). Expanding on this model, it was investigated to what extent different MW free PEGs could restore the prolonged circulation of PLD in the presence of APA. Specifically, APA was intravenously injected in to mice, injected free PEG of various sizes 23.5 hours later, and finally administered PLD 0.5 hours after the free PEG (FIG. 2A). The time at which PLD was injected is referred to as t=0 hr.

Figure 2B:
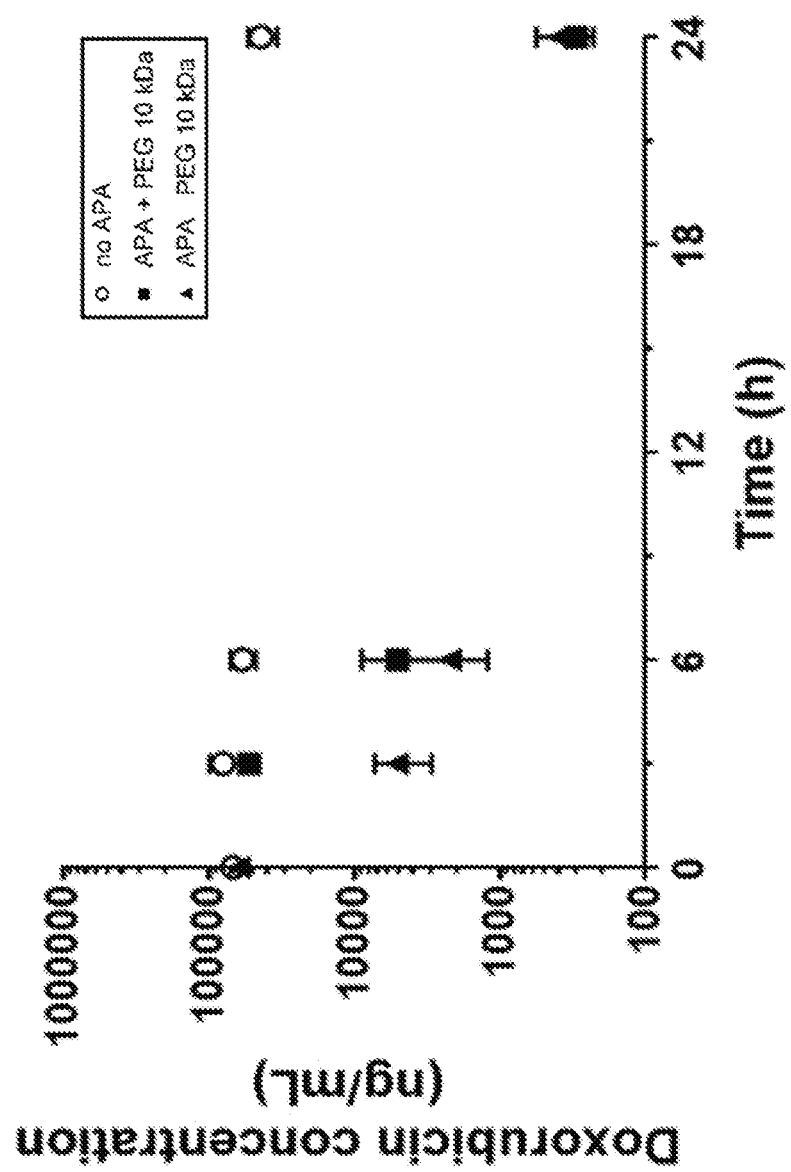
FIG. 2B) shows encapsulated doxorubicin concentration in plasma samples taken from mice that have +/−APA, and +/−PEG 10 kDa prior to PLD administration.

10 kDa PEG, which is within the MW range of sizes used to PEGylate drugs, was evaluated first. It was found that 10 kDa PEG was capable of providing a short reversal of the effects of APA: through 3 hours-post injection (FIG. 2B). With APA concentrations representing induced humoral responses (7 ug/mL), the preinfusion of 10 kDa free PEG was able to increase the mean plasma encapsulated doxorubicin concentrations 10-fold, from 5,116 ng/mL in the saline-treated control to 53,076 ng/mL in the free PEG-treated arm. By the 6-hour timepoint, however, the measured doxorubicin concentrations in mice treated with free PEG 10 kDa were only 2.5-fold higher, at 5,089 ng/mL vs. 2,088 ng/mL in controls. For comparison, control mice that did not have APA still had 59,000 ng/mL doxorubicin in plasma at 6 hours. The limited duration of its effect was most likely due to rapid renal clearance of free PEG as 10 kDa PEG has a terminal half-life of ~18 minutes in mice (See, Yamaoka, T., Y. Tabata, and Y. Ikada, Distribution and tissue uptake of poly(ethylene glycol) with different molecular weights after intravenous administration to mice. J Pharm Sci, 1994. 83(4): p. 601-6). Thus, 3 hours following the administration of PLD, the fraction of the initial dose of 10 kDa PEG (2200 mg/kg, roughly 56 mg in a 25 g mouse) remaining in circulation would be reduced by ~50-fold and inadequate for sustained competitive inhibition of APA accumulating on PLD.

Figure 2C:
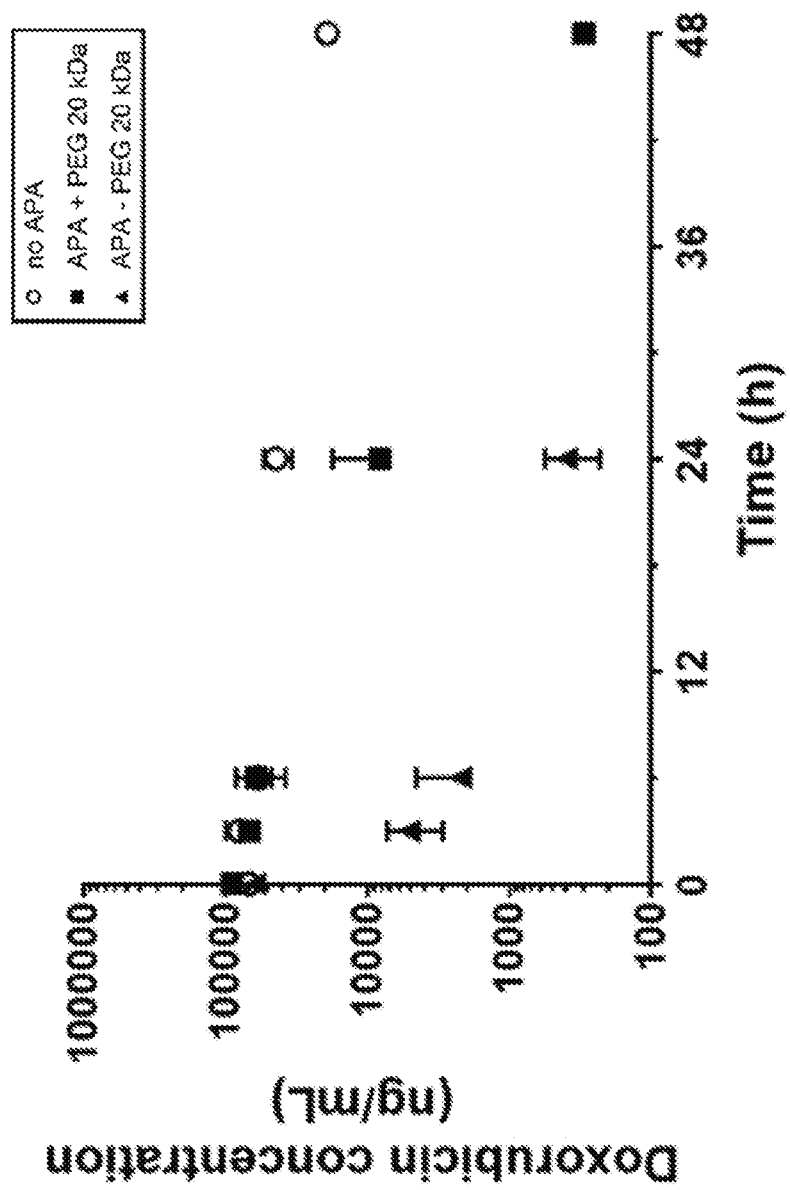
FIG. 2 shows that the administration of free PEG diminishes accelerated blood clearance in mice with anti-PEG antibodies.
FIG. 2(A) shows a schematic of the in vivo study injection schedule.
Figure 2D:
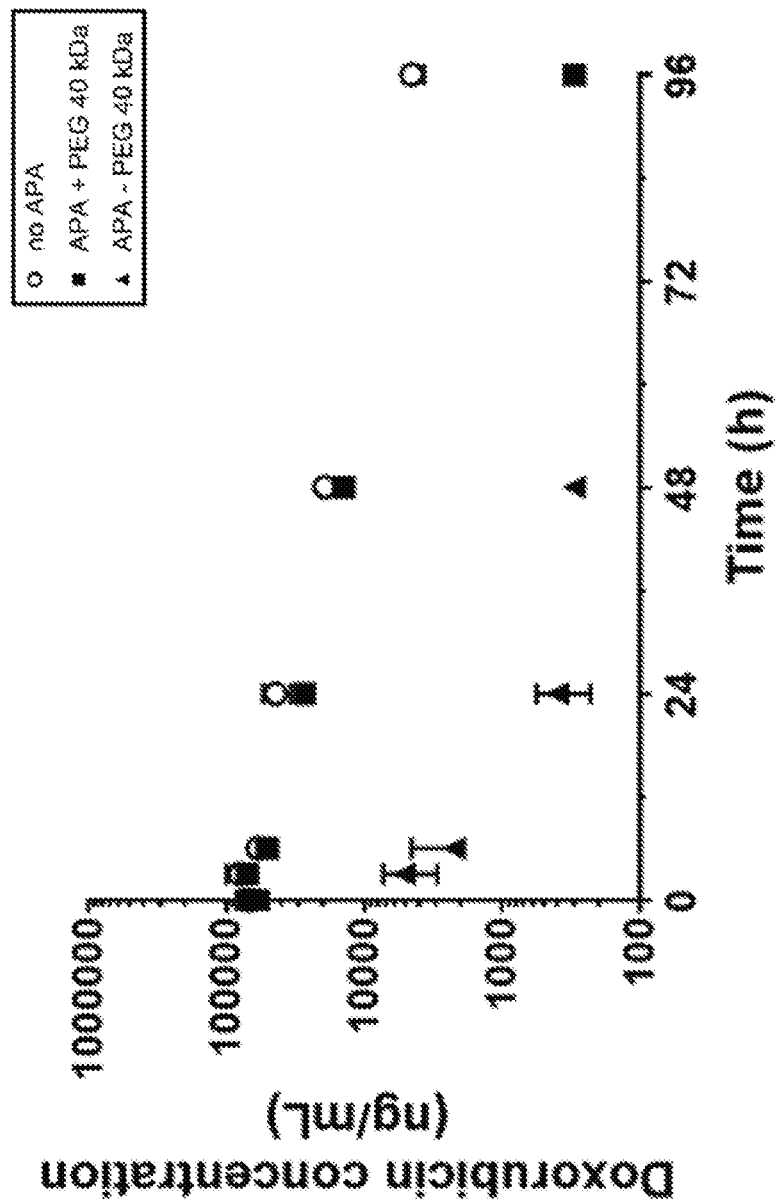
Figure 3A:
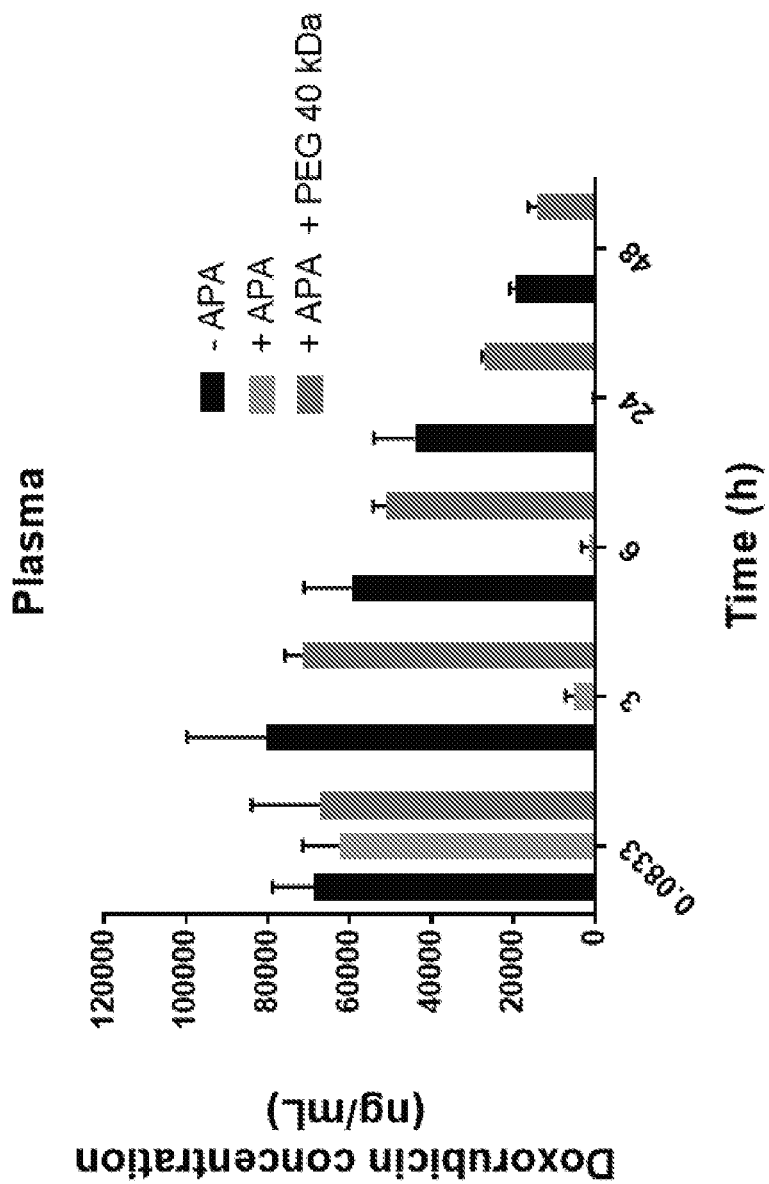
FIG. 3(A)-(D) shows the biodistribution of PLD in the presence and absence of APA and free PEG 40 kDa in plasma, liver, spleen, and lung.
Figure 3B:
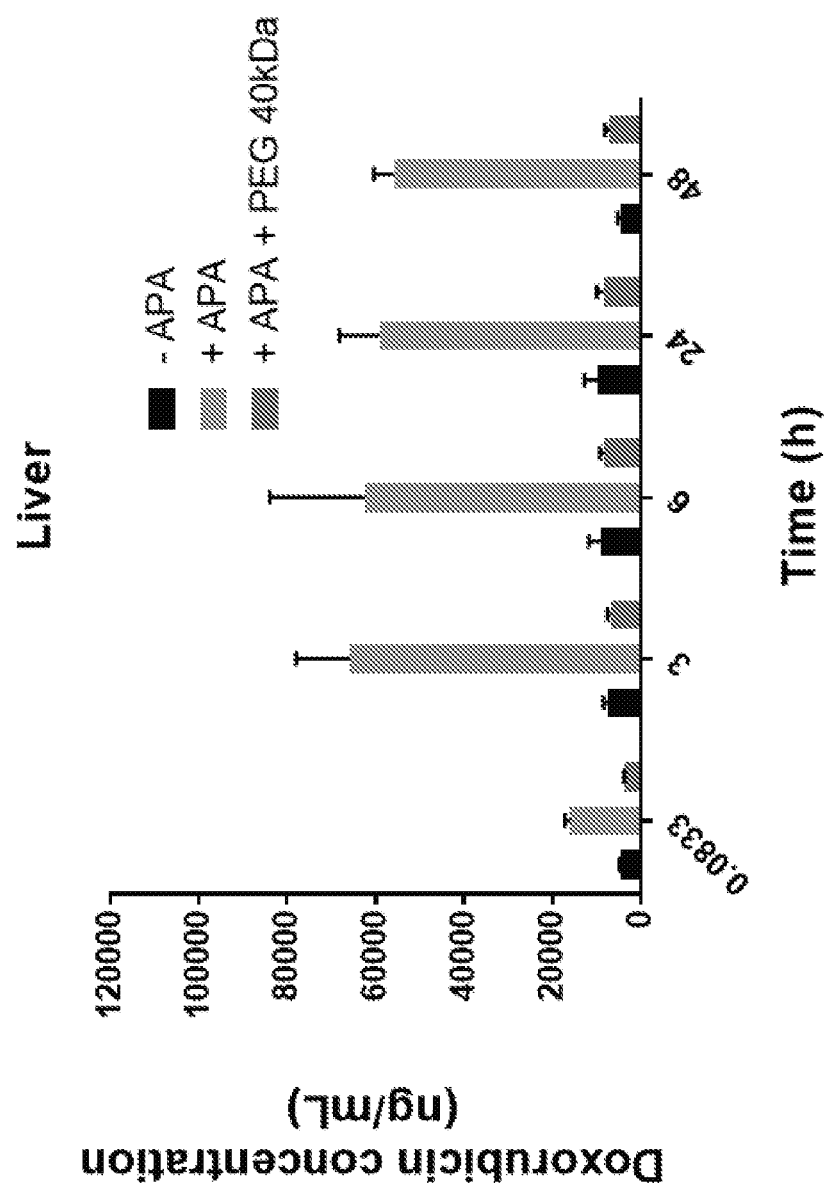
Figure 3C:
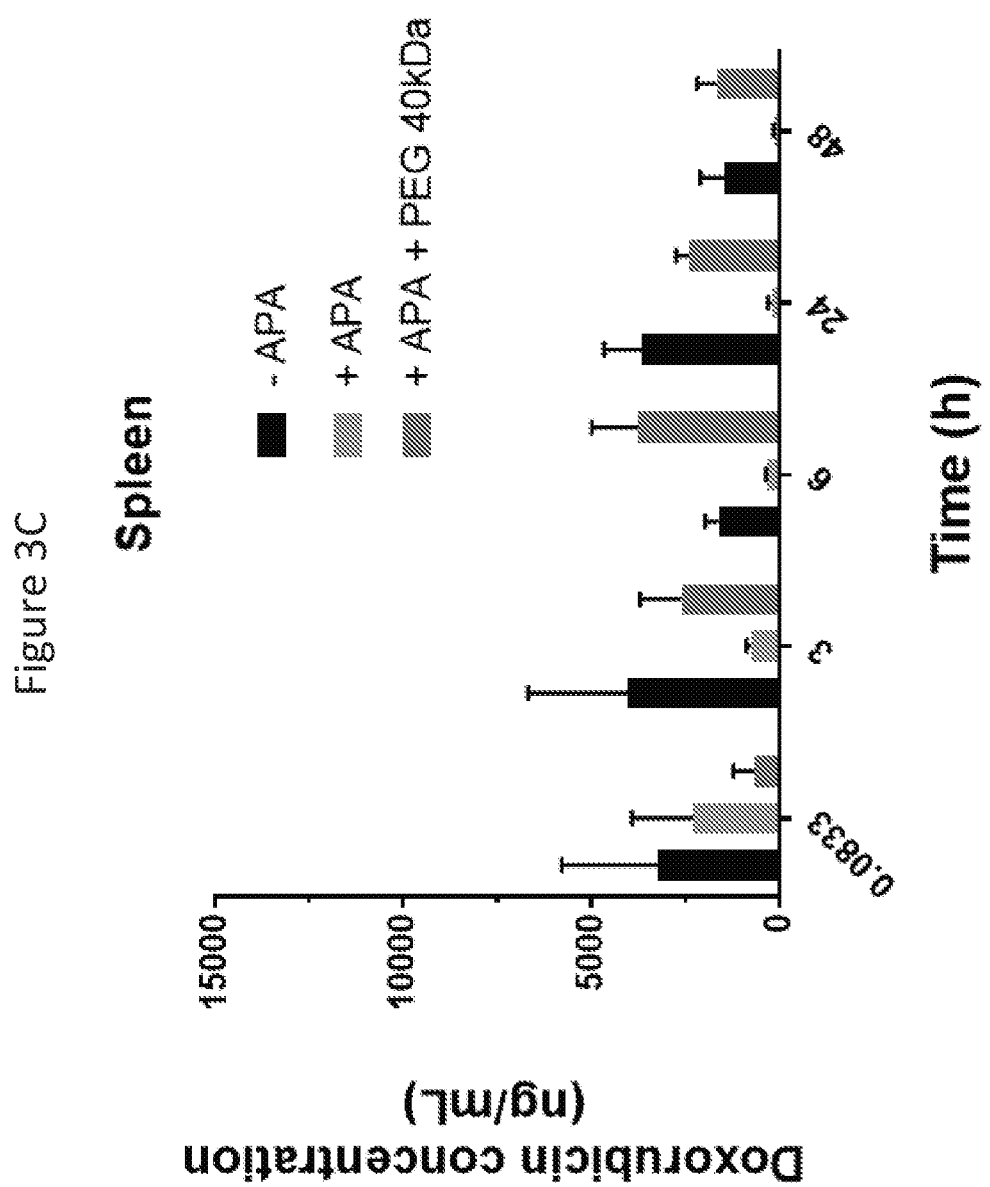
Figure 3D:
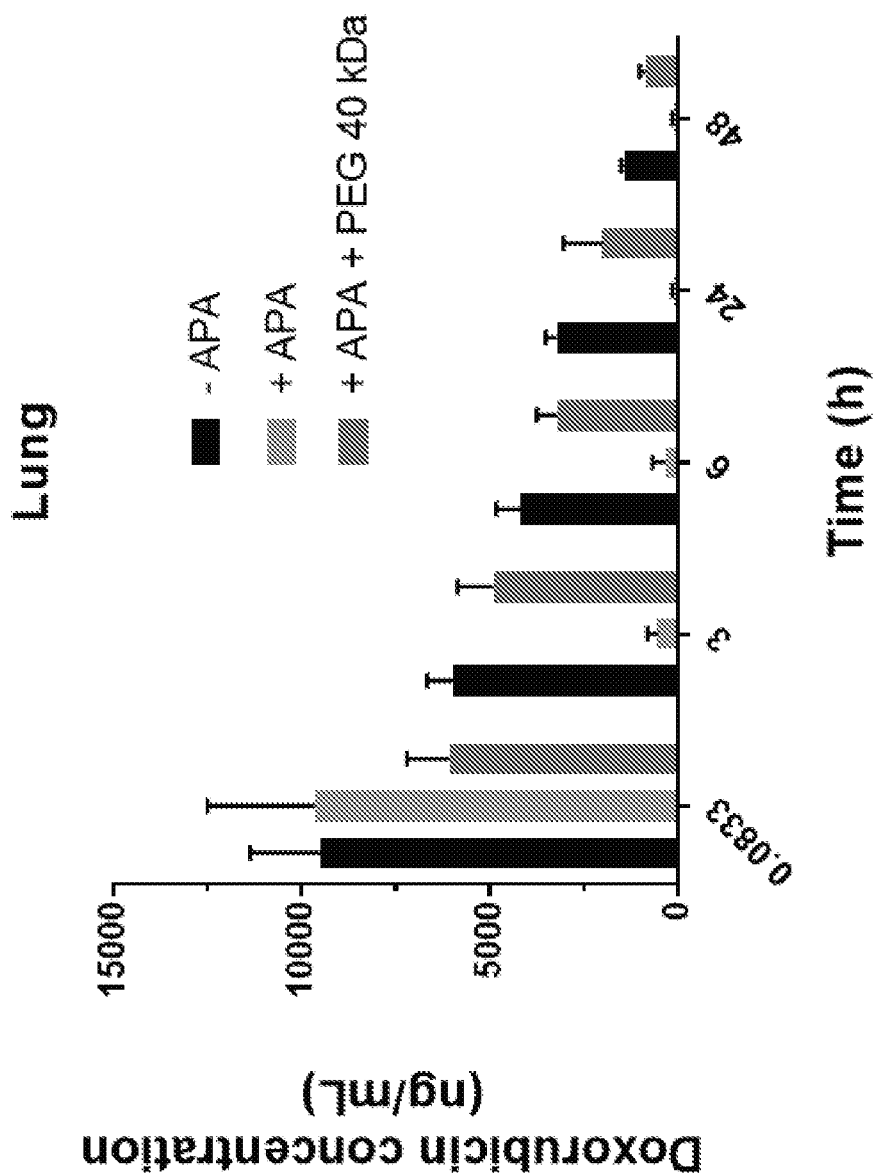

Next, 20 kDa and 40 kDa free PEG, which possess markedly longer elimination half-lives of 3 hours and 15 hours in mice, respectively, were tested (Id.). Consistent with their prolonged circulation, both 20 and 40 kDa free PEG provided much longer reversal of the effects of high titers of APA, effectively rescuing PLD's circulation through 24 and 48 hours, respectively (FIGS. 2C and 3D). Over these time ranges, PLD concentrations in free PEG-treated mice were indistinguishable from controls lacking APA. The administration of free PEG was found to markedly improved the total systemic exposure of PLD in mice. Animals that received free PEG 10 kDa, 20 kDa, and 40 kDa benefited from 3×, 10×, and 20×increases in AUC relative to mice that had APA but were not given free PEG (FIG. 2). This enhanced exposure would be expected to be of particular importance for therapeutics whose primary mechanism of action is to degrade specific compounds found in the plasma, as in the case of pegloticase, pegaspargase, pegarginase, etc.

Figure 4:
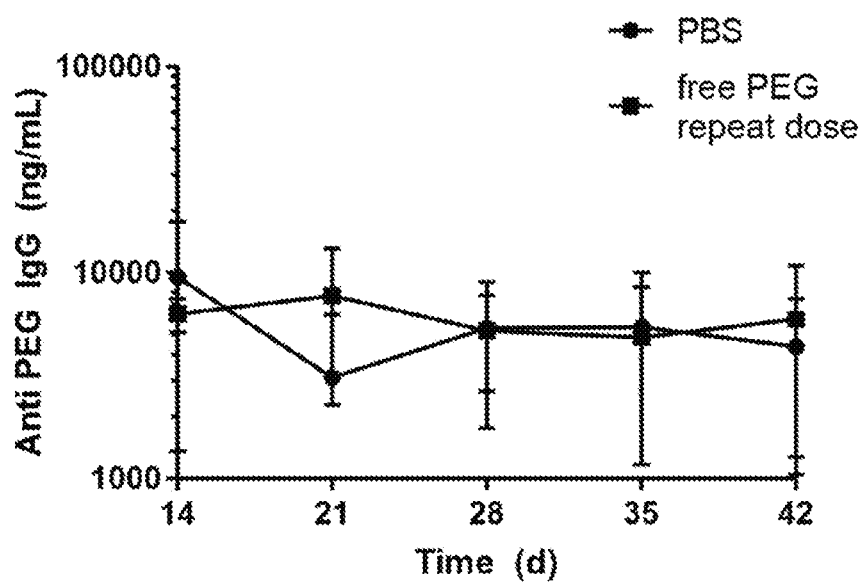
FIG. 4 shows the repeated administration of free PEG to sensitized or naive mice does not lead to runaway (i.e. continuously increasing) APA production.
Figure 4:
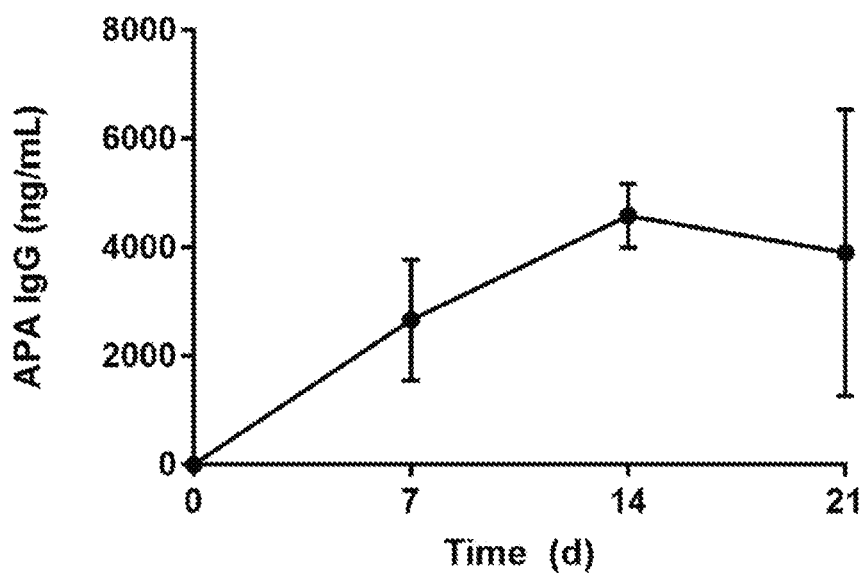
Figure 5:
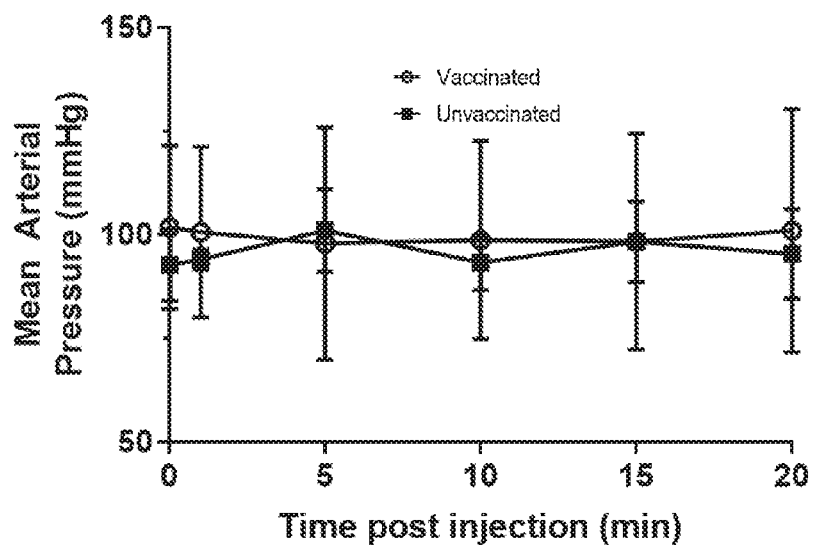
FIG. 5 shows that the administration of free PEG to sensitized or PEG-naive animals does not produce apparent acute toxicity.
Figure 5:
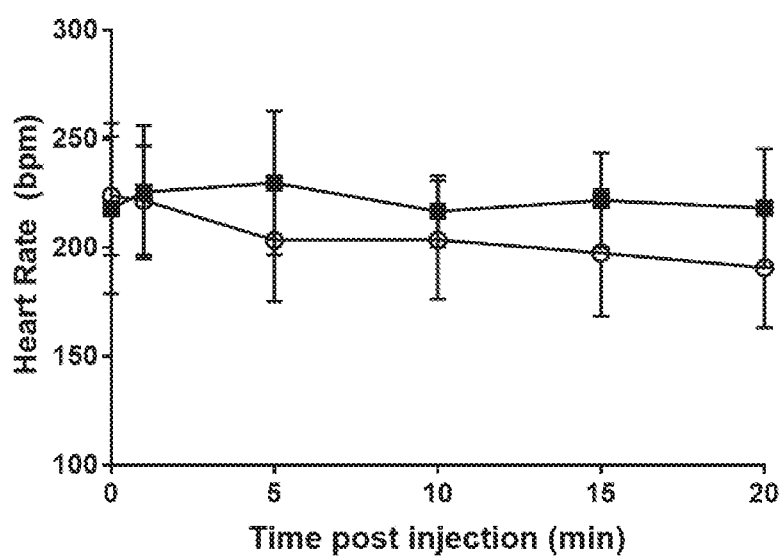

Free PEG Delays the APA-Mediated Hepatic Accumulation of PEG-Liposomes, but does not Alter their Terminal Distribution Profile In mice with no APA, PEGylated drug particles typically exhibit a tendency toward hepatic accumulation, with spleen as the second leading site of accumulation (McSweeney, M. D., et al., A minimal physiologically based pharmacokinetic model that predicts anti-PEG IgG-mediated clearance of PEGylated drugs in human and mouse. Journal of Controlled Release, 2018. 284: p. 171-178.). It was previously found that mice with high levels of APA exhibited greatly increased hepatic but reduced splenic and pulmonary distribution. In order to investigate whether the administration of free PEG would alter this biodistribution pattern, the total doxorubicin concentrations was measured in the liver, spleen, and lungs of mice with high titers of APA dosed with different MW free PEG. It was found that 10 kDa, 20 kDa, and 40 kDa free PEG only delay the hepatic accumulation of PLD, and that by 3, 24, or 96 hours, respectively, eventually the vast majority of the PLD is found in the liver (FIG. 4C).

Free PEG Administration to Sensitized Mice does not Result in Apparent Systemic, Cardiac, Hepatic, or Renal Toxicity There is concern whether introducing free PEG in the presence of high titers of APA would result in PEG/APA immune complexes that could trigger significant renal and systemic toxicities. For example, in systemic lupus erythematosus, and several other autoimmune diseases, the deposition of immune complexes in the kidneys leads to inflammation and glomerular disease (See, Toong, C., S. Adelstein, and T.G. Phan, Clearing the complexity: immune complexes and their treatment in lupus nephritis. International Journal of Nephrology and Renovascular Disease, 2011. 4: p. 17-28.). Thus, it was next sought to determine whether free PEG might lead to prohibitive pathologies. Given that the primary route of elimination of free PEG is renal, a series of tests were first conducted to assess potential damage to the kidneys. In particular, evidence of membranous glomerular nephropathy, i.e. immune complex deposition in the functional space of renal excretion which could lead to glomerular dysfunction was tested. To do so, free PEG 20 kDawas administered to mice that had previously been given APA via intravenous injection. Following the dose of free PEG, mice were sacrificed, and their kidneys were flash-frozen and prepared using standard immunohistochemical methods. No discernable difference in the deposition of IgG, IgM, or complement protein C3 in the glomerular spaces of mice receiving repeated injections of free PEG or PBS (FIG. 6) was observed, suggesting that there is little risk of membranous glomerulonephropathy.

To gain further insight into the potential toxicity profile resulting from using free PEG in the presence of APA, blood and urine samples were also collected following the injection of free PEG 20 kDa, PEG 40 kDa, or PBS in mice with/without APA, and a complete blood count as well as serum tests performed on these samples (Tables 1 and 2). No concerning differences between treated vs. control mice) were found. Since PEGylated proteins have previously been shown to accumulate in the liver, serum albumin concentration, as well as AST and ALT, were also measured, as potential markers of hepatic pathology. No evidence of liver pathology through these systemic markers (Tables 1 and 2) or through histopathologic analysis (FIG. 1) were found.

TABLE 1

PEG 20 kDa (in mice injected with APA)

|  | PBS + PBS (n = 10) | APA + PEG (n = 10) | p-value |
|---|---|---|---|
| Complete Blood Coun |  |  |  |
| Red blood | 10.8 | 10.6 | 0.08 |
| Hemoglobin (g/dL) | 16.6 | 16.3 | 0.12 |
| Hematocrit (%) | 48.7 | 47.7 | 0.15 |
| MCV (fL) | 44.5 | 45.1 | 0.56 |
| Platelet (K/uL) | 114.4 | 113.4 | 0.96 |
| Reticulocyte (K/uL) | 457.7 | 477.4 | 0.54 |
| WBC (K/uL) | 6.3 | 6.8 | 0.46 |
| Neutrophil # | 1.3 | 1.4 | 0.56 |
| Lymphocyte # | 4.5 | 5.0 | 0.39 |
| Serum |  |  |  |
| Creatinine (mg/dL) | 0.38 | 0.39 | 0.91 |
| Albumin (g/dL) | 2.9 | 3.0 | 0.68 |
| BUN (mg/dL) | 22.1 | 21.8 | 0.83 |
| Urine |  |  |  |
| Creatinine (mg/dL) | 65.2 | 64.5 | 0.92 |
| Total protein | 203.1 | 161.3 | 0.10 |

TABLE 2

PEG 40 kDa (in vaccinated mice)

|  | vax + PBS (n = 5) | vax + PEG (n = 9) | p-value |
|---|---|---|---|
| Complete Blood Coun |  |  |  |
| Red blood | 10.3 | 10.2 | 0.7 |
| Hemoglobin (g/dL) | 16.3 | 15.6 | 0.17 |
| Hematocrit (%) | 49.7 | 47.6 | 0.14 |
| MCV (fL) | 48.1 | 46.5 | 0.002 |
| Platelet (K/uL) | 77 | 131.22 | 0.461 |
| Reticulocyte (K/uL) | 446.1 | 523.97 | 0.427 |
| WBC (K/uL) | 4.82 | 4.62 | 0.758 |
| Neutrophil # | 0.9 | 1.03 | 0.702 |
| Lymphocyte # | 3.4 | 3.38 | 0.970 |

TABLE 2-continued

| PEG 40 kDa (in vaccinated mice) | | | |
|---|---|---|---|
| | vax + PBS (n = 5) | vax + PEG (n = 9) | p-value |
| Serum | | | |
| Creatinine (mg/dL) | 0.1 | 0.1 | 0.86 |
| Total protein | 4.9 | 5.0 | 0.22 |
| BUN (mg/dL) | 19.2 | 20.8 | 0.03 |
| ALT (U/L) | 31.8 | 32.3 | 0.977 |
| AST (U/L) | 179.8 | 103.1 | 0.066 |
| Urine (n = 8PEG. 5 PBS | | | |
| Creatinine (mg/dL) | 70.7 | 54.1 | 0.157 |
| Total protein | 200.6 | 93.6 | 0.090 |

The injection of free PEG 20 kDa as a low volume resuscitation (LVR) solution has recently shown efficacy in preclinical models of hypovolemic shock within 20 minutes of administration (See, Plant, V., et al., Low-Volume Resuscitation for Hemorrhagic Shock: Understanding the Mechanism of PEG-20k. J Pharmacol Exp Ther, 2017. 361(2): p. 334-340; Plant, V., et al., Low-volume resuscitation using polyethylene glycol-20k in a preclinical porcine model of hemorrhagic shock. J Trauma Acute Care Surg, 2016. 81(6): p. 1056-1062). Given that free PEG was administered to normotensive animals, it was sought to determine whether this treatment would cause an osmotically-driven increase in the blood pressure of treated animals. Free PEG or PBS was administered to mice, half of which had been vaccinated against PEG, and continuously measured their arterial blood pressure for a period of 20 minutes. No measurable change in the blood pressure or heart rate of mice (Figure was found. In summary, no form of acute toxicity resulting from the administration of free PEG to sensitized or naive mice was detected.

Figure 7:
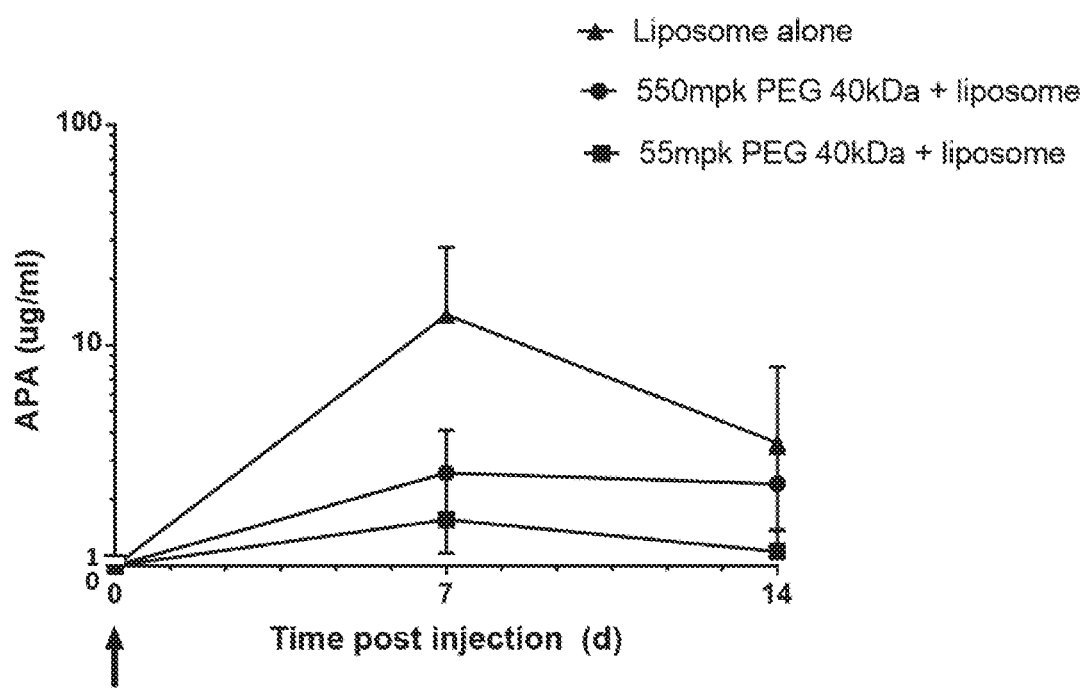
FIG. 7 shows that the administration of free PEG prior to a dose of PEGylated particles leads to attenuation of the induced APA response.

The Prophylactic Administration of Free PEG Attenuates the Antibody Response to Subsequently Administered PEG-Drugs The experimental data has suggested (See FIG. 7) that the administration of free PEG is less immunogenic than the administration of PEGylated particles. On their own, PEGylated liposomes are well known for their capacity to induce anti-PEG antibodies and subsequent accelerated blood clearance. To determine whether the prophylactic administration of free PEG could lessen the intensity of the immune response produced in response to subsequently-administered PEGylated particles, the concentrations of anti-PEG antibodies in mice that received an intravenous injection of PBS (control) or free PEG 40 kDa (550 mg/kg or 55 mg/kg) 30 minutes in advance of PEGylated liposomes were compared. Seven days after the injections, mice that received a prophylactic dose of free PEG had approximately 10-fold lower concentration of anti-PEG antibodies relative to the control mice that did not receive free PEG (FIG. 7).

Free PEG does not Cause Runaway Production of APA Upon Chronic Dosing to Vaccinated or Unvaccinated Mice The common paradigm in immunology is that antigen-specific B cells would respond to the introduction of their corresponding antigens, secreting more antigen-specific antibodies. These additional antibodies are meant to neutralize harmful foreign entities, but unfortunately can result in uncontrolled hypersensitive reactions. To determine if free PEG triggers elevated APA production, free PEG (550 mg/kg) or PBS was administered to naive and vaccinated mice weekly for six weeks, with a blood sample taken immediately prior to each weekly PEG injection as well as at the end of the study to quantify APA levels. In the mice previously vaccinated against PEG, the repeated administration of free PEG did not cause APA concentrations to increase over time (FIG. 4A). Indeed, vaccinated mice that received weekly free PEG injections had APA concentrations indistinguishable from those that received weekly injections of saline. In non-vaccinated mice, while the administration of free PEG did initially induce the generation of low-titers of APA, the APA concentration did not increase further over time with repeated injections (FIG. 4B). Based upon our earlier studies, the concentration of APA induced by the repeated injection of free PEG to naive mice (~4 ug/mL, FIG. 4B) is readily saturated by the therapeutic dose of 40 kDa free PEG. These results suggest that the induction of APA by free PEG alone is likely limited in scope and can be managed through the continued use of free PEG.

It is understood that the foregoing detailed description and accompanying examples are merely illustrative and are not to be taken as limitations upon the scope of the disclosure, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

For reasons of completeness, various aspects of the disclosure are set out in the following numbered clauses:

1. A method of reducing accelerated blood clearance of at least one pegylated therapeutic composition by anti-PEG antibodies in a subject suffering from a disease and in need of treatment thereof, the method comprising the steps of:
   administering from about 0.1 to about 500 milligrams per kilogram of at least one high molecular weight polyethylene glycol composition to a subject suffering from a disease and in need of treatment with at least one pegylated therapeutic composition,
   wherein the high molecular weight polyethylene glycol comprises at least one high molecular weight polyethylene glycol having a molecular weight of between about 20 kDa to about 200 kDa, and
   further wherein the high molecular weight polyethylene glycol composition is administered prior to or simultaneously with the administration of the at least one pegylated therapeutic composition.

2. The method of clause 1, wherein the at least one high molecular weight polyethylene glycol composition is administered in an amount of 0.5 to about 400 milligrams per kilogram.

3. The method of any of clauses 1 or 2, wherein the at least one high molecular weight polyethylene glycol composition is administered in an amount of 1.0 to about 250 milligrams per kilogram.

4. The method of any one of clauses 1-3, wherein the at least one high molecular weight polyethylene glycol has a molecular weight of about 20 kDa, about 25 kDa, about 30 kDa, about 40 kDa, about 50 kDa, about 60 kDa, about 70 kDa, about 75 kDa, about 80 kDa, about 90 kDa, about 100 kDa, about 110 kDa, about 120 kDa, about 130 kDa, about 140 kDa, about 150 kDa, about 160 kDa, about 170 kDa, about 180 kDa, about 190 kDa, about 200 kDa or combinations thereof.

5. The method of any one of clauses 1-4, wherein the at least one high molecular weight polyethylene glycol has a geometry that is linear, branched, star-shaped or comb-shaped.

6. The method of any one of clauses 1-5, wherein the at least one high molecule weight polyethylene glycol composition is administered prior to the subject being administered the at least one pegylated therapeutic composition.

7. The method of any one of clauses 1-6, wherein the high molecular weight polyethylene glycol composition is administered at least 30 seconds, at least 60 seconds, at least 90 seconds, at least 2 minutes, at least 3 minutes, at least 4 minutes, at least 5 minutes, at least 10 minutes, at least 15 minutes, at least 20 minutes, at least 25 minutes, at least 30 minutes, at least 40 minutes, at least 45 minutes, at least 50 minutes, at least 60 minutes, at least 90 minutes, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours prior to administration of the at least one pegylated therapeutic composition.

8. The method of any one of clauses 1-7, wherein the at least one pegylated therapeutic composition comprises at least one protein, peptide, antibody, enzyme, liposome, aptamer, dendrimer, polymeric particle, micelle, inorganic nanoparticle or combinations thereof.

9. The method of clause 8, wherein the antibody is a monoclonal antibody, a chimeric antibody, a humanized antibody, a fully human antibody, a bi-specific antibody, a multi-specific antibody, an antibody fragment, or combinations thereof.

10. The method of clauses 1-5 and 8-9, wherein the at least one high molecular weight polyethylene glycol composition is administered simultaneously with the at least one pegylated therapeutic composition.

11. The method of clause 10, wherein the at least one high molecular weight polyethylene glycol composition is co-administered with the at least one pegylated therapeutic composition.

12. A method of increasing the circulation half-life of at least one pegylated therapeutic composition to be repeatedly administered to a subject suffering from a disease, the method comprising the step of:
    administering from about 1 to about 2500 milligrams per kilogram of at least one high molecular weight polyethylene glycol composition to a subject that has previously been administered at least one pegylated therapeutic composition or that is known to possess a high titer of pre-existing anti-PEG antibodies,
    wherein the high molecular weight polyethylene glycol composition comprises at least one high molecular weight polyethylene glycol having a molecular weight of between about 20 kDa to about 200 kDa, and
    wherein the high molecular weight polyethylene glycol composition is administered prior to or simultaneously with any subsequent or further administration of the at least one pegylated therapeutic composition to the subject.

13. The method of clause 12, wherein the at least one high molecular weight polyethylene glycol composition is administered in an amount of 50 to about 2200 milligrams per kilogram.

14. The method of any of clauses 12 or 13, wherein the at least one high molecular weight polyethylene glycol composition is administered in an amount of 100 to about 2000 milligrams per kilogram.

15. The method of any one of clauses 12-14, wherein the at least one high molecular weight polyethylene glycol has a molecular weight of about 20 kDa, about 25 kDa, about 30 kDa, about 40 kDa, about 50 kDa, about 60 kDa, about 70 kDa, about 75 kDa, about 80 kDa, about 90 kDa, about 100 kDa, about 110 kDa, about 120 kDa, about 130 kDa, about 140 kDa, about 150 kDa, about 160 kDa, about 170 kDa, about 180 kDa, about 190 kDa, about 200 kDa or combinations thereof.

16. The method of any one of clauses 12-15, wherein the at least one high molecular weight polyethylene glycol has a geometry that is linear, branched, star-shaped or comb-shaped.

17. The method of any one of clauses 12-16, wherein the at least one high molecule weight polyethylene glycol composition is administered prior to the subject receiving any further administration of the at least one pegylated therapeutic composition.

18. The method of any one of clauses 12-17, wherein the high molecular weight polyethylene glycol composition is administered at least 30 seconds, at least 60 seconds, at least 90 seconds, at least 2 minutes, at least 3 minutes, at least 4 minutes, at least 5 minutes, at least 10 minutes, at least 15 minutes, at least 20 minutes, at least 25 minutes, at least 30 minutes, at least 40 minutes, at least 45 minutes, at least 50 minutes, at least 60 minutes, at least 90 minutes, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours prior to administration of the at least one pegylated therapeutic composition.

19. The method of any one of clauses 12-18, wherein the at least one pegylated therapeutic composition comprises at least one protein, peptide, antibody, enzyme, liposome, aptamer, dendrimer, polymeric particle, micelle, inorganic nanoparticle or combinations thereof.

20. The method of clause 19, wherein the antibody is a monoclonal antibody, a chimeric antibody, a humanized antibody, a fully human antibody, a bi-specific antibody, a multi-specific antibody, an antibody fragment, or combinations thereof.

21. The method of clauses 12-16 and 19-20, wherein the at least one high molecular weight polyethylene glycol composition is administered simultaneously with the at least one pegylated therapeutic composition.

22. The method of clause 21, wherein the at least one high molecular weight polyethylene glycol composition is co-administered with the at least one pegylated therapeutic composition.

23. A method of restoring the pharmacokinetics of at least one pegylated therapeutic composition that will be repeatedly administered to a subject suffering from a disease, the method comprising the step of:
    administering from about 1 to about 2500 milligrams per kilogram of at least one high molecular weight polyethylene glycol composition to a subject that has previously been administered at least one pegylated therapeutic composition,
    wherein the high molecular weight polyethylene glycol composition comprises at least one high molecular weight polyethylene glycol having a molecular weight of between about 20 kDa to about 200 kDa, wherein the high molecular weight polyethylene glycol composition is administered prior to or simultaneously with any subsequent or further administration of at least one pegylated therapeutic composition to the subject, further wherein the high molecular weight polyethylene glycol composition reduces the binding of anti-polyethylene glycol antibodies to the at least one pegylated therapeutic composition, and still further wherein the administration of the at least one high molecular weight polyethylene glycol composition restores the pharmacokinetics of the at least one pegylated therapeutic composition.

24. The method of clause 23, wherein the subject has a high titer of anti-polyethylene glycol antibodies.

25. The method of clause 23, wherein the at least one pegylated therapeutic composition has an improved circulation half-life.

26. The method of clause 23, wherein the at least one high molecular weight polyethylene glycol composition is administered in an amount of 50 to about 2200 milligrams per kilogram.

27. The method of any of clauses 23-26, wherein the at least one high molecular weight polyethylene glycol composition is administered in an amount of 100 to about 2000 milligrams per kilogram.

28. The method of any one of clauses 23-27, wherein the at least one high molecular weight polyethylene glycol has a molecular weight of about 20 kDa, about 25 kDa, about 30 kDa, about 40 kDa, about 50 kDa, about 60 kDa, about 70 kDa, about 75 kDa, about 80 kDa, about 90 kDa, about 100 kDa, about 110 kDa, about 120 kDa, about 130 kDa, about 140 kDa, about 150 kDa, about 160 kDa, about 170 kDa, about 180 kDa, about 190 kDa, about 200 kDa or combinations thereof.

29. The method of any one of clauses 23-28, wherein the at least one high molecular weight polyethylene glycol has a geometry that is linear, branched, star-shaped or comb-shaped.

30. The method of any one of clauses 23-29, wherein the at least one high molecule weight polyethylene glycol composition is administered prior to the subject receiving any further administration of the at least one pegylated therapeutic composition.

31. The method of any one of clauses 23-30, wherein the high molecular weight polyethylene glycol composition is administered at least 30 seconds, at least 60 seconds, at least 90 seconds, at least 2 minutes, at least 3 minutes, at least 4 minutes, at least 5 minutes, at least 10 minutes, at least 15 minutes, at least 20 minutes, at least 25 minutes, at least 30 minutes, at least 40 minutes, at least 45 minutes, at least 50 minutes, at least 60 minutes, at least 90 minutes, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours prior to administration of the at least one pegylated therapeutic composition.

32. The method of any one of clauses 23-31, wherein the at least one pegylated therapeutic composition comprises at least one protein, peptide, antibody, enzyme, liposome, aptamer, dendrimer, polymeric particle, micelle, inorganic nanoparticle or combinations thereof.

33. The method of clause 32, wherein the antibody is a monoclonal antibody, a chimeric antibody, a humanized antibody, a fully human antibody, a bi-specific antibody, a multi-specific antibody, an antibody fragment, or combinations thereof.

34. The method of clauses 23-29 and 32-33, wherein the at least one high molecular weight polyethylene glycol composition is administered simultaneously with the at least one pegylated therapeutic composition.

35. The method of clause 34, wherein the at least one high molecular weight polyethylene glycol composition is co-administered with the at least one pegylated therapeutic composition.

36. A method of reducing the formation of anti-PEG antibodies in a suffering from a disease and in need of treatment or continued treatment thereof, the method comprising the step of:

administering from about 1 to about 2500 milligrams per kilogram of at least one high molecular weight polyethylene glycol composition, about 10 to 2500 milligrams per kilogram of at least one low molecular weight polyethylene glycol composition or about 10 to 2500 milligrams per kilogram of a combination of at least one high molecular weight polyethylene glycol composition and at least one low molecular weight polyethylene glycol composition to a subject that either has previously not been administered at least one pegylated therapeutic composition or that has previously been administered at least one pegylated therapeutic composition, wherein the high molecular weight polyethylene glycol composition comprises at least one high molecular weight polyethylene glycol having a molecular weight of between about 20 kDa to about 200 kDa, wherein the low molecular weight polyethylene glycol composition comprises at least one high molecular weight polyethylene glycol having a molecular weight of between about 200 Da to about 19 kDa, 37. The method of clause 36, wherein the at least one high molecular weight polyethylene glycol composition, at least one low molecular weight polyethylene glycol composition or combination of at least one high molecular weight polyethylene glycol composition and at least one low molecular weight polyethylene glycol composition is administered in an amount of 50 to about 2200 milligrams per kilogram.

38. The method of any of clauses 36-37, wherein at least one high molecular weight polyethylene glycol composition, at least one low molecular weight polyethylene glycol composition or combination of at least one high molecular weight polyethylene glycol composition and at least one low molecular weight polyethylene glycol composition is administered in an amount of 100 to about 2000 milligrams per kilogram.

39. The method of any one of clauses 36-38, wherein the at least one high molecular weight polyethylene glycol composition, at least one low molecular weight polyethylene glycol composition or combination of at least one high molecular weight polyethylene glycol composition and at least one low molecular weight polyethylene glycol composition is administered prior to the subject receiving any treatment with at least one pegylated therapeutic composition.

40. The method of any one of clauses 36-38, wherein at least one high molecular weight polyethylene glycol composition, at least one low molecular weight polyethylene glycol composition or combination of at least one high molecular weight polyethylene glycol composition and at least one low molecular weight polyethylene glycol composition is administered prior to the subject receiving any further administration of the at least one pegylated therapeutic composition.

41. The method of any one of clauses 36-40, wherein the at least one high molecular weight polyethylene glycol composition, at least one low molecular weight polyethylene glycol composition or combination of at least one high molecular weight polyethylene glycol composition and at least one low molecular weight polyethylene glycol composition is administered at least 30 seconds, at least 60 seconds, at least 90 seconds, at least 2 minutes, at least 3 minutes, at least 4 minutes, at least 5 minutes, at least 10 minutes, at least 15 minutes, at least 20 minutes, at least 25 minutes, at least 30 minutes, at least 40 minutes, at least 45 minutes, at least 50 minutes, at least 60 minutes, at least 90 minutes, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours or at least 24 hours prior to administration of the at least one pegylated therapeutic composition.

42. The method of any one of clauses 36-41, wherein the at least one pegylated therapeutic composition comprises at least one protein, peptide, antibody, enzyme, liposome, aptamer, dendrimer, polymeric particle, micelle, inorganic nanoparticle or combinations thereof.

43. The method of clause 42, wherein the antibody is a monoclonal antibody, a chimeric antibody, a humanized antibody, a fully human antibody, a bi-specific antibody, a multi-specific antibody, an antibody fragment, or combinations thereof.

44. The method of clauses 36-43, wherein the at least one high molecular weight polyethylene glycol composition, at least one low molecular weight polyethylene glycol composition or combination of at least one high molecular weight polyethylene glycol composition and at least one low molecular weight polyethylene glycol composition is administered simultaneously with the at least one pegylated therapeutic composition.

45. The method of clause 44, wherein the at least one high molecular weight polyethylene glycol composition, at least one low molecular weight polyethylene glycol composition or combination of at least one high molecular weight polyethylene glycol composition and at least one low molecular weight polyethylene glycol composition is co-administered with the at least one pegylated therapeutic composition.

What is claimed is:

1. A method of reducing accelerated blood clearance of at least one pegylated therapeutic composition by anti-PEG antibodies in a subject suffering from a disease and in need of treatment thereof, the method comprising the steps of:
   administering from 0.1 to 500 milligrams per kilogram of at least one high molecular weight polyethylene glycol composition to a subject suffering from a disease and in need of treatment with at least one pegylated therapeutic composition,
   wherein the high molecular weight polyethylene glycol composition comprises high molecular weight polyethylene glycol having a molecular weight of between 20 kDa to 200 kDa, and
   further wherein the high molecular weight polyethylene glycol composition is administered 30 minutes prior to or simultaneously with the administration of the at least one pegylated therapeutic composition.

2. The method of claim 1, wherein the at least one high molecular weight polyethylene glycol composition is administered in an amount of 0.5 to about 400 milligrams per kilogram.

3. The method of claim 1, wherein the at least one high molecular weight polyethylene glycol composition is administered in an amount of 1.0 to about 250 milligrams per kilogram.

4. The method of claim 1, wherein the at least one high molecular weight polyethylene glycol has a molecular weight of about 20 kDa, about 25 kDa, about 30 kDa, about 40 kDa, about 50 kDa, about 60 kDa, about 70 kDa, about 75 kDa, about kDa, about 90 kDa, about 100 kDa, about 110 kDa, about 120 kDa, about 130 kDa, about 140 kDa, about 150 kDa, about 160 kDa, about 170 kDa, about 180 kDa, about 190 kDa, about 200 kDa or combinations thereof.

5. The method of claim 1, wherein the at least one high molecular weight polyethylene glycol has a geometry that is linear, star-shaped or comb-shaped.

6. The method of claim 1, wherein the at least one high molecule weight polyethylene glycol composition is administered prior to the subject being administered the at least one pegylated therapeutic composition.

7. The method of claim 1, wherein the at least one pegylated therapeutic composition comprises at least one protein, peptide, antibody, enzyme, liposome, aptamer, dendrimer, polymeric particle, micelle, inorganic nanoparticle or combinations thereof.

8. The method of claim 7, wherein the antibody is a monoclonal antibody, a chimeric antibody, a humanized antibody, a fully human antibody, a bi-specific antibody, a multi-specific antibody, an antibody fragment, or combinations thereof.

9. The method of claim 1, wherein the at least one high molecular weight polyethylene glycol composition is administered simultaneously with the at least one pegylated therapeutic composition.

10. The method of claim 9, wherein the at least one high molecular weight polyethylene glycol composition is co-administered with the at least one pegylated therapeutic composition as a single formulation or composition.

11. The method of claim 1, wherein the high molecular weight polyethylene glycol composition is a linear high molecular weight polyethylene glycol having a molecular weight of between 20 kDa to 200 kDa.

12. The method of claim 1, wherein the high molecular weight polyethylene glycol composition comprises high molecular weight polyethylene glycol having a molecular weight of between 25 kDa to 200 kDa.

13. A method of reducing accelerated blood clearance of at least one pegylated therapeutic composition by anti-PEG antibodies in a subject suffering from a disease and in need of treatment thereof, the method comprising the steps of:
   administering from 0.1 to 500 milligrams per kilogram of a linear high molecular weight polyethylene glycol composition to a subject suffering from a disease and in need of treatment with at least one pegylated therapeutic composition,
   wherein the linear high molecular weight polyethylene glycol composition has a molecular weight of between 20 kDa to 200 kDa of the polyethylene glycol, and
   further wherein the high molecular weight polyethylene glycol composition is administered prior to or simultaneously with the administration of the at least one pegylated therapeutic composition.

14. A method of reducing accelerated blood clearance of at least one pegylated therapeutic composition by anti-PEG antibodies in a subject suffering from a disease and in need of treatment thereof, the method comprising the steps of:

administering from 0.1 to 500 milligrams per kilogram of a linear high molecular weight polyethylene glycol composition to a subject suffering from a disease and in need of treatment with at least one pegylated therapeutic composition, wherein the linear high molecular weight polyethylene glycol composition has a molecular weight of between 25 kDa to 200 kDa of the polyethylene glycol, and further wherein the high molecular weight polyethylene glycol composition is administered 30 minutes prior to or simultaneously with the administration of the at least one pegylated therapeutic composition.

\* \* \* \* \*

UNITED STATES PATENT AND TRADEMARK OFFICE
CERTIFICATE OF CORRECTION

| | | |
|---|---|---|
| PATENT NO. | : 11,813,333 B2 | Page 1 of 1 |
| APPLICATION NO. | : 16/642722 | |
| DATED | : November 14, 2023 | |
| INVENTOR(S) | : Samuel Lai and Morgan McSweeney | |

It is certified that error appears in the above-identified patent and that said Letters Patent is hereby corrected as shown below:

In the Claims

Claim 4, Column 56, Line 15 reads:
"75 kDa, about kDa, about 90 kDa, about 100 kDa, about 110;"

Whereas it should read:
-- 75 kDa, about 80 kDa, about 90 kDa, about 100 kDa, about 110; --

Signed and Sealed this
Ninth Day of July, 2024

Katherine Kelly Vidal
*Director of the United States Patent and Trademark Office*